(12) United States Patent
Dhar et al.

(10) Patent No.: US 9,517,277 B2
(45) Date of Patent: Dec. 13, 2016

(54) IMMUNE-STIMULATING PHOTOACTIVE HYBRID NANOPARTICLES

(75) Inventors: Shanta Dhar, Athens, GA (US); Joshua Choi, Athens, GA (US); Sean Marrache, Athens, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 158 days.

(21) Appl. No.: 14/128,238

(22) PCT Filed: Jul. 11, 2012

(86) PCT No.: PCT/US2012/046171
§ 371 (c)(1),
(2), (4) Date: Dec. 20, 2013

(87) PCT Pub. No.: WO2013/012628
PCT Pub. Date: Jan. 24, 2013

(65) Prior Publication Data
US 2014/0220143 A1 Aug. 7, 2014

Related U.S. Application Data

(60) Provisional application No. 61/508,242, filed on Jul. 15, 2011.

(51) Int. Cl.
| A61K 51/00 | (2006.01) |
| A61M 36/14 | (2006.01) |
| A61K 47/48 | (2006.01) |
| A61K 41/00 | (2006.01) |

(52) U.S. Cl.
CPC ..... *A61K 47/48915* (2013.01); *A61K 41/0071* (2013.01)

(58) Field of Classification Search
CPC .... A61K 49/00; A61K 49/0021; A61K 41/00; A61K 41/0057; A61K 49/001; A61K 41/0071; A61K 49/0015; A61K 49/0017; A61K 49/0036; A61K 49/0065; A61K 2121/00; A61K 2123/00
USPC .... 424/1.11, 1.29, 1.33, 9.1, 9.2, 9.6, 184.1, 424/278.1, 400, 1.37, 489, 490; 977/773
See application file for complete search history.

(56) References Cited

U.S. PATENT DOCUMENTS

| 7,850,981 B2 * | 12/2010 | Curry ................ A61K 41/0057 424/278.1 |
| 2005/0187207 A1 | 8/2005 | Curry et al. |
| 2009/0062719 A1 | 3/2009 | Neuberger |

FOREIGN PATENT DOCUMENTS

| WO | 2011049256 A1 | 4/2011 |
| WO | 2011071970 A2 | 6/2011 |

OTHER PUBLICATIONS

Demberelnyamba et al, Int. J. Mol. Sci., 2008, vol. 9, pp. 864-871.*
The International Search Report and Written Opinion dated Jan. 29, 2013.

* cited by examiner

*Primary Examiner* — D L Jones
(74) *Attorney, Agent, or Firm* — Thomas|Horstemeyer, LLP

(57) ABSTRACT

Provides is a therapeutic technology that combines the phototoxic and immune-stimulating ability of photodynamic therapy with the widespread effectiveness of the immune system to reduce the viability of such as cancer cells and tumors. The nanoparticle compositions of the disclosure combine an immunostimulant with a photosensitizer using a nanoparticle delivery platform. For example, zinc pthalocyanine, which is a long-wavelength absorbing photosensitizer, integrated into a polymeric nanoparticle core made up of poly(D,L-lactic-co-glycolic acid)-b-poly(ethylene glycol) (PLGA-b-PEG). The outside surface of the core can be coated with metallic nanoparticles, which are then modified with CpG-ODN. Metastatic mouse breast carcinoma cells showed significant photocytotoxicity of the hybrid after irradiation with a 660 nm LASER light and this activity was remarkably better than either treatment alone. Treatment of mouse bone marrow derived dendritic cells with the photodynamic therapy-killed 4T1 cell lysate showed that the combination of photodynamic therapy with a synergistic immunostimulant in a single nanoparticle system resulted in an immune response suitable for the treatment of such as a metastatic cancer.

3 Claims, 14 Drawing Sheets

| wt% of ZnPc | Diameter (nm) | PDI | Zeta Potential (mV) | %Loading |
|---|---|---|---|---|
| 0 | 92±1 | 0.33±0.01 | 16.0±3.5 | 0 |
| 5 | 104±7 | 0.36±0.06 | 3.8±2.4 | 3 |
| 10 | 101.0±0.5 | 0.27±0.01 | 17.6±0.5 | 8 |
| 20 | 117±10 | 0.25±0.01 | 9.0±1.4 | 20 |
| 30 | 120±6 | 0.29±0.07 | 6.9±3.3 | 20 |

```
                     SEQUENCE LISTING

<160> NUMBER OF SEQ ID NOS: 1

<210> SEQ ID NO 1
<211> LENGTH: 20
<212> TYPE: DNA
<213> ORGANISM: Artificial sequence
<220> FEATURE:
<223> OTHER INFORMATION: CpG-ODN Oligonucleotide

<400> SEQUENCE: 1
tccatgacgt tcctgacgtt                                             20
```

IMMUNE-STIMULATING PHOTOACTIVE HYBRID NANOPARTICLES

CROSS-REFERENCE TO RELATED APPLICATIONS

This application is the 35 U.S.C. §371 national stage of PCT application having serial number PCT/US2012/046141, filed on Jul. 11, 2012. This application also claims priority to U.S. Provisional Application Ser. No. 61/508,242, filed on Jul. 15, 2011, which is entirely incorporated herein by reference.

STATEMENT ON FUNDING PROVIDED BY THE U.S. GOVERNMENT

This invention was made with government support under NIH Grant No.: P30 GM092378 awarded by the U.S. National Institutes of Health of the United States government. The government has certain rights in the invention.

SEQUENCE LISTING

The present disclosure includes a sequence listing incorporated herein by reference in its entirety.

FIELD OF THE DISCLOSURE

This disclosure relates to hybrid nanoparticles for the delivery of a photodynamic therapy agent and an immunostimulants to a cell. The disclosure further relates to the use of the hybrid nanoparticles for reducing the viability of a cancer cell.

BACKGROUND

The management of metastatic breast cancer remains a therapeutic challenge (DeSantis et al., (2011) Ca-Cancer J. Clin. 61: 409-418). An ideal cancer treatment should not only cause tumor regression and eradication but also induce a systemic antitumor immunity for control of metastatic tumors and long-term tumor resistance. This can be achieved by using the immune system as a weapon to recognize the tumor antigen so that once the primary tumor is eliminated, metastases will also be destroyed. Earlier success in applying the immune system to metastatic cancer, as well as the limited contributions from conventional chemo or radiation therapy makes metastatic cancer a focus for contemporary development of novel treatment options (Turcotte& Rosenberg (2011) Adv. Surg. 45: 341-360). The main pillars of cancer treatment chemotherapy, surgery, and radiation therapy are known to suppress the immune system (Castano et al., (2006) Nat. Rev. Cancer. 6: 535-545). The only cancer treatment that stimulates anti-tumor immunity is photodynamic therapy (PDT) (Castano et al., (2006) Nat. Rev. Cancer 6: 535-545; Gollnick et al., (2006) Laser Surg. Med. 38: 509-515). Photodynamic therapy involves administration of a photosensitizer (PS) followed by illumination of the tumor with a long wavelength (600-800 nm) light producing reactive oxygen species (ROS) resulting in vascular shutdown, cancer cell apoptosis, and the induction of a host immune response (Dougherty et al (1998) J. Natl. Cancer Inst. 90: 889-905). The exact mechanism involved in the PDT-mediated induction of anti-tumor immunity is not yet understood. Possible mechanisms include alterations in the tumor microenvironment by stimulating pro-inflammatory cytokines and direct effects of photodynamic therapy on the tumor that increases immunogenicity (Castano et al., (2006) Nat. Rev. Cancer. 6: 535-545). Photodynamic therapy can increase dendritic cells (DC) maturation and differentiation, which leads to the generation of tumor specific cytotoxic CD8 T cells that can destroy distant deposits of untreated tumor (FIG. 1) (Castano et al., (2006) Nat. Rev. Cancer. 6: 535-545; M. Korbelik, (2011) Photoch. Photobio. Sci. 10: 664-669; van Duijnhoven et al., (2003) Photochem. Photobiol. 78: 235-240; A. Oseroff (2006) J. Invest. Dermatol. 126: 542-544).

There are increasing number of studies showing that immunoadjuvants when injected intratumorally can produce a similar infiltration of leukocytes into the tumor (Castano et al., (2006) Nat. Rev. Cancer. 6: 535-545). Immunoadjuvants are frequently prepared from microbial cells and are thought to act via Toll-like receptors (TLRs) (Werling & Jungi (2003) Vet Immunol. Immunopathol. 91: 1-12) present on macrophages and dendritic cells (DCs). This indicates that a combination of photodynamic therapy with a DC activating agent that can act as an agonist of TLR might be promising for the treatment of metastatic tumor. There are few reports of combinations of photodynamic therapy with microbial derived products potentiating tumor response and leading to long-term anti-tumor immunity (Castano et al., (2006) Nat. Rev. Cancer. 6: 535-545; Gollnick & Brackett (2010) Immunol. Res. 46: 216-226). However, thus far administrating the immunoadjuvants as separate constructs by intratumoral injection has only been explored to combine photodynamic therapy with immunotherapy (Qiang et al., (2008) Med. Res. Rev. 8. 632-644; T. G. St Denis (2011) Photoch. Photobio. Sci 10. 792-801). Nanotechnology-based differential combination therapy can be emphasized as a promising strategy for metastatic breast cancer.

SUMMARY

The disclosure provides a therapeutic technology that combines the phototoxic and immune-stimulating ability of photodynamic therapy (PDT) with the widespread effectiveness of the immune system to treat cancer such as, but not limited to, metastatic breast cancer. The nanoparticle compositions of the disclosure combine an immunostimulant with a photosensitizer using a nanoparticle delivery platform. For example, zinc pthalocyanine, which is a long-wavelength absorbing photosensitizer, integrated into a polymeric nanoparticle core made up of poly(D,L-lactic-co-glycolic acid)-b-poly(ethylene glycol) (PLGA-b-PEG). The outside surface of the core was coated with the metallic nanoparticles, which were then modified with CpG-ODN.

Metastatic mouse breast carcinoma cells showed significant photocytotoxicity of the hybrid nanoparticles of the disclosure after irradiation with a 660 nm LASER light and this activity was remarkably better than either treatment alone. Treatment of mouse bone marrow derived dendritic cells with the photodynamic therapy-killed 4T1 cell lysate showed that the combination of photodynamic therapy with a synergistic immunostimulant in a single nanoparticle system resulted in an immune response suitable for the treatment of metastatic cancer.

One aspect of the disclosure encompasses embodiments of a multifunctional hybrid nanoparticle, the hybrid nanoparticle comprising: a nanoparticle core comprising a photosensitizer and a polymer; a plurality of metallic nanoparticles disposed on the surface of the nanoparticle core; and an immunostimulant disposed on the plurality of metallic nanoparticles.

In embodiments of this aspect of the disclosure, the photosensitizer can produce an activated oxygen species when irradiated with a light energy.

In embodiments of this aspect of the disclosure, the photosensitizer can be selected from the group consisting of: a porphyrin, a chlorophyll, a dye, a metallosensitizer, a quantum dot, or any combination thereof.

In embodiments of this aspect of the disclosure, the photosensitizer can be selected from the group consisting of: aminolevulinic acid (ALA), silicon phthalocyanine Pc 4, m-tetrahydroxyphenylchlorin (mTHPC), mono-L-aspartyl chlorin e6 (NPe6), tris-(2,3-naphthalocyanato)bis-chloro-aluminium(III), tris-(2,3-naphthalocyanato)bis-chlorozinc (II), and (zinc(II) phthalocyanine (ZnPc)).

In embodiments of this aspect of the disclosure, the polymer of the nanoparticle core can be biodegradable, and wherein the photosensitizer is embedded in the polymer or the photosensitizer is encapsulated by the polymer, or disposed on the surface of a polymer nanoparticle.

In some embodiments of this aspect of the disclosure, the nanoparticle core can comprise a polymer of poly (D,L-lactic-co-glycolic acid)-b-poly(ethylene glycol), and can further comprise a plurality of functional groups exposed at the surface of the nanoparticle core and capable of receiving the metallic nanoparticles thereon. In these embodiments, the functional groups exposed at the surface of the nanoparticle core and capable of receiving the metallic nanoparticles thereon can comprise PEG-amine moieties extending from the surface of the nanoparticle core.

In embodiments of this aspect of the disclosure, the metallic nanoparticles can be gold nanoparticles, silver nanoparticles, copper nanoparticles, nickel nanoparticles, ferrous nanoparticles, or any combination thereof.

In some embodiments of this aspect of the disclosure, the metallic nanoparticles are gold nanoparticles.

In embodiments of this aspect of the disclosure, the immunostimulant disposed on the metallic nanoparticles can be selected from the group consisting of: a CpG-ODN, aTLR4 agonist monophosphoryl lipid A, a CpG (TLR9) or adenosine derivative thereof, an RNA comprising a poly-U or GU-rich sequence, an imidazoquinoline, and a guanosine analogues that stimulates TLR7/8.

In embodiments of this aspect of the disclosure, the immunostimulant can be disposed on the metallic nanoparticles non-covalently.

In embodiments of this aspect of the disclosure, the immunostimulant is disposed on the metallic nanoparticles covalently.

In embodiments of this aspect of the disclosure, the immunostimulant is disposed on the metallic nanoparticles by a linker moiety.

In embodiments of this aspect of the disclosure, the linker moiety is cleavable, thereby releasing the immunostimulant from the multifunctional hybrid nanoparticle.

In embodiments of this aspect of the disclosure, the CpG-ODN comprises a phosphorothioate backbone.

In some embodiments of this aspect of the disclosure, the photosensitizer is zinc pthalocyanine, the nanoparticle core comprises a biodegradable polymer of poly (D,L-lactic-co-glycolic acid)-b-poly(ethylene glycol), the metallic nanoparticles are gold nanoparticles, and the immunostimulant disposed on the metallic nanoparticles is a CpG-ODN.

Another aspect of the disclosure encompasses embodiments of a method of reducing the viability of a cell comprising the steps of: (i) administering to an animal or human subject a pharmaceutically acceptable composition comprising a multifunctional hybrid nanoparticle comprising a nanoparticle core comprising a photosensitizer and a polymer, a plurality of metallic nanoparticles disposed on the surface of the nanoparticle core; and an immunostimulant disposed on the metallic nanoparticles, and where the immunostimulant generates an immune response in the animal or human subject that reduces the viability of a cell or population of cells in the subject; and (ii) irradiating the cell with a light energy having a wavelength generating a photoactivated species by the photosensitizer.

In embodiments of this aspect of the disclosure, the photosensitizer is zinc pthalocyanine, the nanoparticle core comprises a biodegradable polymer of poly (D,L-lactic-co-glycolic acid)-b-poly(ethylene glycol), the metallic nanoparticles are gold nanoparticles, and the immunostimulant disposed on the metallic nanoparticles is a CpG-ODN, wherein the photosensitizer produces activated oxygen species.

In embodiments of this aspect of the disclosure, the cell or population of cells is a cancerous cell or a tumor.

Yet another aspect of the disclosure encompasses embodiments of a pharmaceutically acceptable composition comprising a multifunctional hybrid nanoparticle comprising a nanoparticle core comprising a photosensitizer and a polymer; a plurality of a metallic nanoparticle disposed on the surface of the nanoparticle core; and an immunostimulant disposed on the surfaces of the plurality of metallic nanoparticles; and a pharmaceutically acceptable carrier.

In some embodiments of this aspect of the disclosure, the photosensitizer can be zinc pthalocyanine, the nanoparticle core can comprise a biodegradable polymer of poly (D,L-lactic-co-glycolic acid)-b-poly(ethylene glycol), the metallic nanoparticles are gold nanoparticles, and the immunostimulant disposed on the metallic nanoparticles is a CpG-ODN, where the photosensitizer produces activated oxygen species.

BRIEF DESCRIPTION OF THE FIGURES

Many aspects of the disclosure can be better understood with reference to the following figures.

FIG. 2A illustrates schematically a nanoparticle platform of the disclosure where the immunostimulants (immunoadjuvants) are attached to the gold nanoparticles noncovalently.

FIG. 2B illustrates schematically a nanoparticle platform of the disclosure where the immunostimulants (immunoadjuvants) are attached to the gold nanoparticles covalently.

FIG. 4A is a series of digital images of NP suspensions showing no visible aggregation.

FIG. 4B is a series of digital TEM images of ZnPc-Poly-NPs, Au—ZnPc-Poly-NPs, and CpG-ODN-Au—ZnPc-Poly-NPs.

FIG. 4C illustrates the characterization of hybrid nanoparticles by UV-Vis spectroscopy.

FIG. 4D is a pair of graphs illustrating the (left) hydrodynamic diameter and (right) zeta potential of the nanoparticles by DLS measurements.

FIG. 4E illustrates the sizes, PDI, zeta potential, and loading of ZnPc in the PLGA-b-PEG-NH$_2$ with varied ZnPc percent weight.

Figure 1:
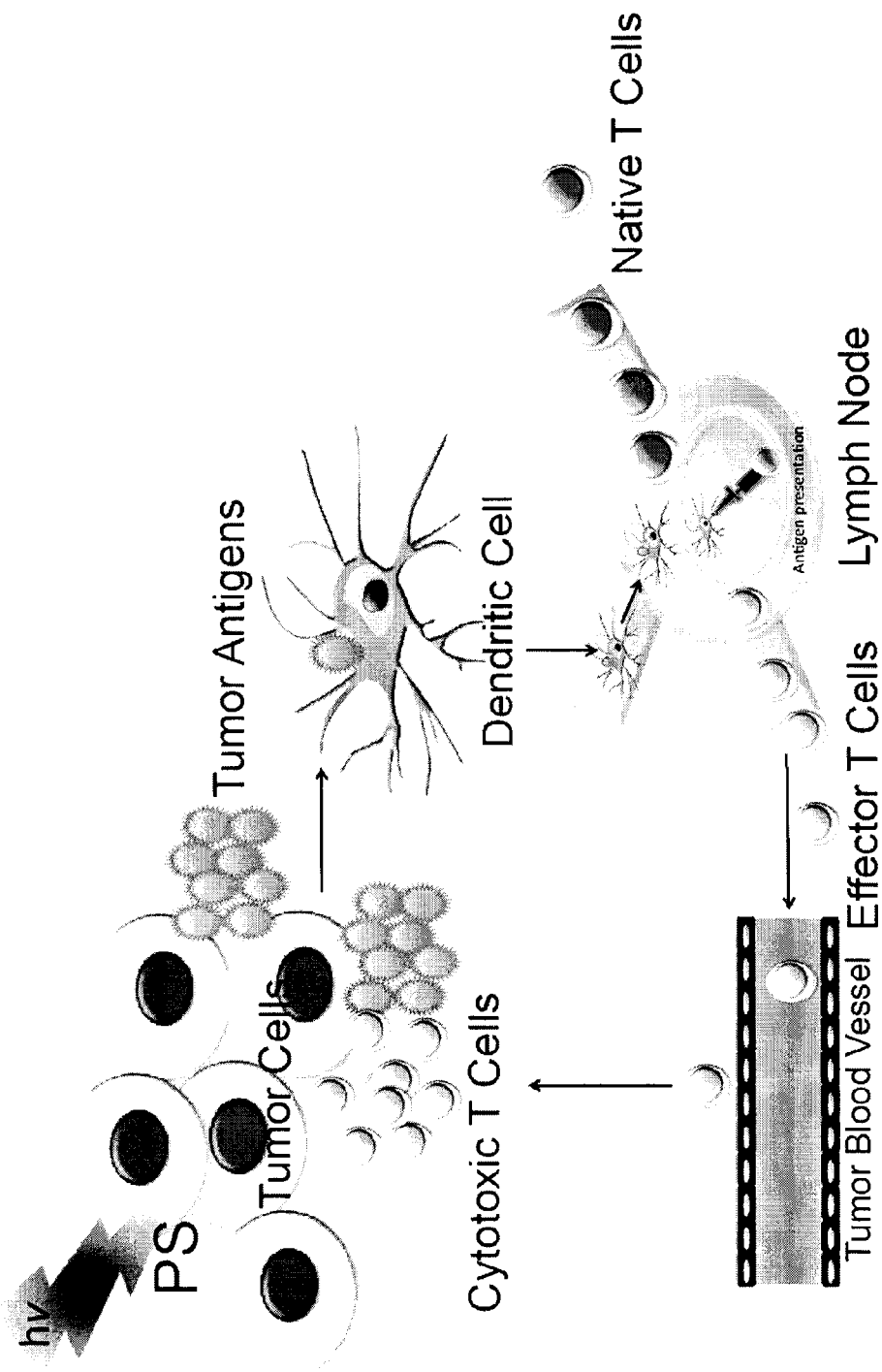
FIG. 1 is a cartoon illustrating the process of phagocytosis of tumor antigens by DCs after PDT.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DESCRIPTION OF THE DISCLOSURE

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those skilled in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent. As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Abbreviations

BMDC: Bone marrow derived dendritic cell; CpG: Unmethylated CpG dinucleotides; DLS: Dynamic light scattering; IL: Interleukins; NP: Nanoparticle; ODNs: Oligodeoxynucleotides; PDT: Photodynamic therapy; PDI:

Polydispersity index; PEG: Polyethylene glycol; PLGA: Poly(lactic-co-glycolic acid); PS: Photosensitizer; TNF: Tumor necrosis factor; ZnPc: Zinc phthalocyanine Definitions The term "cell or population of cells" as used herein refers to an isolated cell or plurality of cells excised from a tissue or grown in vitro by tissue culture techniques. In the alternative, a population of cells may also be a plurality of cells in vivo in a tissue of an animal or human host.

The term "contacting a cell or population of cells" as used herein refers to delivering a composition such as, for example, a probe composition according to the present disclosure with or without a pharmaceutically or physiologically acceptable carrier to an isolated or cultured cell or population of cells, or administering the probe in a suitable pharmaceutically acceptable carrier to an animal or human host. Thereupon, it may be systemically delivered to the target and other tissues of the host, or delivered to a localized target area of the host. Administration may be, but is not limited to, intravenous delivery, intraperitoneal delivery, intramuscularly, subcutaneously or by any other method known in the art. One method is to deliver the composition directly into a blood vessel leading immediately into a target organ or tissue such as a prostate, thereby reducing dilution of the probe in the general circulatory system.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probes and pharmaceutically acceptable carriers preferably should be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

Pharmaceutical compositions and unit dosage forms of the disclosure typically also include one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that include primary or secondary amines are particularly susceptible to such accelerated decomposition.

The disclosure further encompasses pharmaceutical compositions and dosage forms that include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific example of a solubility modulator is tartaric acid.

Like the amounts and types of excipients, the amounts and specific type of active ingredient in a dosage form may differ depending on factors such as, but not limited to, the route by which it is to be administered to patients. However, typical dosage forms of the compounds of the disclosure include a pharmaceutically acceptable salt or salts, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, more preferably in an amount of from 50 mg to 500 mg, even more preferably in an amount of from about 30 mg to about 100 mg.

Additionally, the compounds and/or compositions can be delivered using lipid- or polymer-based nanoparticles. For example, the nanoparticles can be designed to improve the pharmacological and therapeutic properties of drugs administered parenterally (Allen & Cullis (2004) *Science* 303: 1818-1822).

Topical dosage forms of the disclosure include, but are not limited to, creams, lotions, ointments, gels, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms including a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art. See, e.g., Remington's Pharmaceutical Sciences, 18th Ed., Mack Publishing, Easton, Pa. (1990).

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "poly-(D,L-lactic acid)" (PLA) as used herein refers to $(C_3H_4O_2)_n$ Poly(lactic acid) or polylactide (PLA), a thermoplastic aliphatic polyester. PLA is not a polyacid (polyelectrolyte), but rather a polyester. Two lactic acid molecules undergo a single esterification and then catalytically cyclize to form a cyclic lactide ester. PLA of high molecular weight is produced from the dilactate ester by ring-opening polymerization using stannous catalyst. It is understood that several distinct forms of polylactide may be used in the compositions of the disclosure including, but not limited to, poly-L-lactide (PLLA) resulting from polymerization of L,L-lattice (also known as L-lactide), PDLA (poly-D-lactide), and poly(L-lactide-co-D,L-lactide) (PLDLLA).

Also contemplated to be useful in the formation of the microparticles of the disclosure is a poly(lactic-co-glycolic acid) copolymers (PLGA) alone or in combination with a PLA-derivative. PLGA or poly(lactic-co-glycolic acid) is a copolymer synthesized by means of random ring-opening co-polymerization of two different monomers, the cyclic dimers (1,4-dioxane-2,5-diones) of glycolic acid and lactic acid. Common catalysts used in the preparation of this polymer include tin(II) 2-ethylhexanoate, tin(II) alkoxides, or aluminum isopropoxide. During polymerization, successive monomeric units (of glycolic or lactic acid) are linked together in PLGA by ester linkages, thus yielding a linear, aliphatic polyester as a product. Depending on the ratio of lactide to glycolide used for the polymerization, different forms of PLGA can be obtained, such as, but not limited to PLGA 75:25, a copolymer whose composition is 75% lactic acid and 25% glycolic acid). Unlike the homopolymer of lactic acid (polylactide) (PLA) which has poor solubility, PLGA can be dissolved by a wide range of common solvents, including chlorinated solvents, tetrahydrofuran, acetone or ethyl acetate.

The term "photodynamic treatment" as used herein refers to a means for the treatment of a biological target by the photo-induced inactivation of the biological target (and for the treatment of cancer and other diseases. A source of light excites a photosensitizing nanomaterial that in turn generates highly reactive singlet oxygen ($^1O_2$) from non-reactive triplet oxygen molecules ($^3O_2$). A triplet oxygen is the ground state of oxygen.

The term "photosensitizer" as used herein refers to an activatable pharmaceutical agent (alternatively called a "photoactive agent" or PA) and is an agent that normally exists in an inactive state in the absence of an activation signal. When the agent is activated by a matching activation signal under activating conditions, it is capable of effecting the desired pharmacological effect on a target cell (i.e. preferably a predetermined cellular change). Activation of the agent may be as simple as delivering the signal to the agent or may further premise on a set of activation conditions. For example, in the former case, an activatable pharmaceutical agent, such as a photosensitizer, may be activated by UV-A radiation. Once activated, the agent in its active-state may then directly proceed to effect a cellular change.

A wide array of photosensitizers for PDT exist, including porphyrins, chlorophylls and dyes. Some examples include aminolevulinic acid (ALA), silicon phthalocyanine Pc 4, m-tetrahydroxyphenylchlorin (mTHPC), and mono-L-aspartyl chlorin e6 (NPe6). Photosensitizers are commercially available for clinical use include, but are not limited to, ALLUMERA®, PHOTOFRIN®, VISUDYNE®, LEVULAN®, FOSCAN®, METVIX®, HEXVIX®, CYSVIEW®, and LASERPHYRIN®. They all have certain characteristics: high absorption at long wavelengths (tissue is much more transparent at longer wavelengths (approximately 700-850 nm)); high singlet oxygen quantum yield; natural fluorescence; high chemical stability; and low dark toxicity. Photosensitizers suitable for use in the compositions of the disclosure further may include metallosensitizers such as a metallophthalocyanin including, but not limited to, tris-(2,3-naphthalocyanato)bis-chloroaluminium(III) and zinc(II) (zinc(II) phthalocyanine (ZnPc)). The metal of the photosensitizer can be, but is not limited to, zinc, aluminum, nickel, cobalt, copper, vanadium, platinum, ruthenium, iron, or combinations thereof known in the art. Metallophthalocyanins, which are hydrophobic, provide advantageous solubility for encapsulation inside polymeric nanoparticles.

The terms "administration of" and or "administering a" compound should be understood to mean providing a nanoparticle of the disclosure to an individual in need of treatment. The nanoparticles of the present disclosure may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The term "composition" as used herein refers to a product comprising the specified ingredients in the specified amounts, as well as any product which results, directly or indirectly, from combination of the specified ingredients in the specified amounts. Such a term in relation to a pharmaceutical composition is intended to encompass a product comprising the active ingredient(s), and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure and a pharmaceutically acceptable carrier.

The term "cancer:" as used herein shall be given its ordinary meaning and is a general term for diseases in which abnormal cells divide without control. Cancer cells can invade nearby tissues and can spread through the bloodstream and lymphatic system to other parts of the body.

There are several main types of cancer, for example, carcinoma is a cancer that begins in the skin or in tissues that line or cover internal organs. Sarcoma is a cancer that begins in the bone, cartilage, fat, muscle, blood vessels, or other connective or supportive tissue. Leukemia is cancer that starts in blood-forming tissue such as bone marrow, and causes large numbers of abnormal blood cells to be produced and enter the bloodstream. Lymphoma is cancer that begins in the cells of the immune system. The probes and methods of the disclosure are especially advantageous for detecting cancer cells and tumors localized to a specific site in an animal or human, although it is contemplated that the systems may be useful to detect circulating cells.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it with differing processes that have gone awry. Solid tumors may be benign (not cancerous), or malignant (cancerous). Different types of solid tumors are named for the type of cells that form them.

The term "quantum dot" (quantum dots) as used herein refers to semiconductor nanocrystals or artificial atoms, which are semiconductor crystals that contain anywhere between 100 to 1,000 electrons and range from about 2 to about 10 nm. Some quantum dots can be between about 10 to about 20 nm in diameter. Quantum dots have high quantum yields, which makes them particularly useful for optical applications. Quantum dots are fluorophores that fluoresce by forming excitons, which can be thought of as the excited state of traditional fluorophores, but which have much longer lifetimes of up to 200 nanoseconds. This property provides quantum dots with low photobleaching. The energy level of quantum dots can be controlled by changing the size and shape of the quantum dot, and the depth of the quantum dots' potential. One of the optical features of small excitonic quantum dots is coloration, which is determined by the size of the dot. The larger the dot, the redder, or more towards the red end of the spectrum the fluorescence. The smaller the dot, the bluer or more towards the blue end it is. The bandgap energy that determines the energy and hence the color of the fluoresced light is inversely proportional to the square of the size of the quantum dot. Larger quantum dots have more energy levels which are more closely spaced, thus allowing the quantum dot to absorb photons containing less energy, i.e. those closer to the red end of the spectrum. Because the emission frequency of a dot is dependent on the bandgap, it is therefore possible to control the output wavelength of a dot with extreme precision. Colloidally prepared quantum dots are free floating and can be attached to a variety of molecules via metal coordinating functional groups. These groups include but are not limited to thiol, amine, nitrile, phosphine, phosphine oxide, phosphonic acid, carboxylic acids or other ligands. By bonding appropriate molecules to the surface, the quantum dots can be dispersed or dissolved in nearly any solvent or incorporated into a variety of inorganic and organic films.

The synthesis of quantum dots is well known and is described in U.S. Pat. Nos. 5,906,670; 5,888,885; 5,229,320; 5,482,890; 6,468,808; 6,306,736; 6,225,198, etc., International Patent Application WO 03/003015, (all of which are incorporated herein by reference in their entireties) and in many research articles. The wavelengths emitted by quantum dots and other physical and chemical characteristics have been described in U.S. Pat. No. 6,468,808 and International Patent Application WO 03/003015, both of which are incorporated herein by reference in their entireties.

The term "multifunctional hybrid nanoparticle" as used herein refers to a nanoparticle comprising at least two functional moieties. For example, but not intended to be limiting, one functional moiety can be a photosensitizer that under the appropriate irradiating conditions can generate a reactive oxygen species, and a second functional group can be an immunostimulant.

The term "nanoparticle core" as used herein refers to a nanoparticle structure that can have other moieties attached thereto. In some embodiments the nanoparticle core can be a multilayered nanoparticle, or in other embodiments can be a polymeric nanoparticle having a functional moiety distributed throughout the polymeric mass. In either embodiment, the nanoparticle core can have other functional moieties attached thereto.

The term "plurality of metallic nanoparticles" as used herein refers to a population of metallic nanoparticles, which may, but not necessarily, have a diameter smaller than that of the nanoparticle core to which they are attached. The population of metallic nanoparticles may be sufficient in number to be uniformly distributed over the surface of the underlying nanoparticle core, substantially cover the surface, or be non-uniformly distributed over the surface of the nanoparticle core.

The term "activated oxygen species" as used herein refers to a singlet oxygen (or $^1O_2$), an electronically excited state of molecular oxygen ($O_2$) that is less stable than the normal triplet oxygen. Singlet oxygen can persist for over an hour at room temperature, depending on the environment. Singlet oxygen is in the same quantum state as most molecules and thus reacts readily with them, thus making singlet oxygen highly reactive. Singlet oxygen is usually generated with a photosensitizer pigment. In photodynamic therapy, singlet oxygen is produced to kill cancer cells.

The term "functional group" as used herein refers to a chemical group able to interact covalently or non-covalently with another group, molecule, or moiety, thereby forming a bond. In the embodiments of the disclosure, particularly advantageous functional groups are amine groups of PEG-amine molecules extending from the surface of a nanoparticle core. Under physiological conditions, the amine s can form non-covalent bonds with positively charged metallic nanoparticles.

Description

Figure 2A:
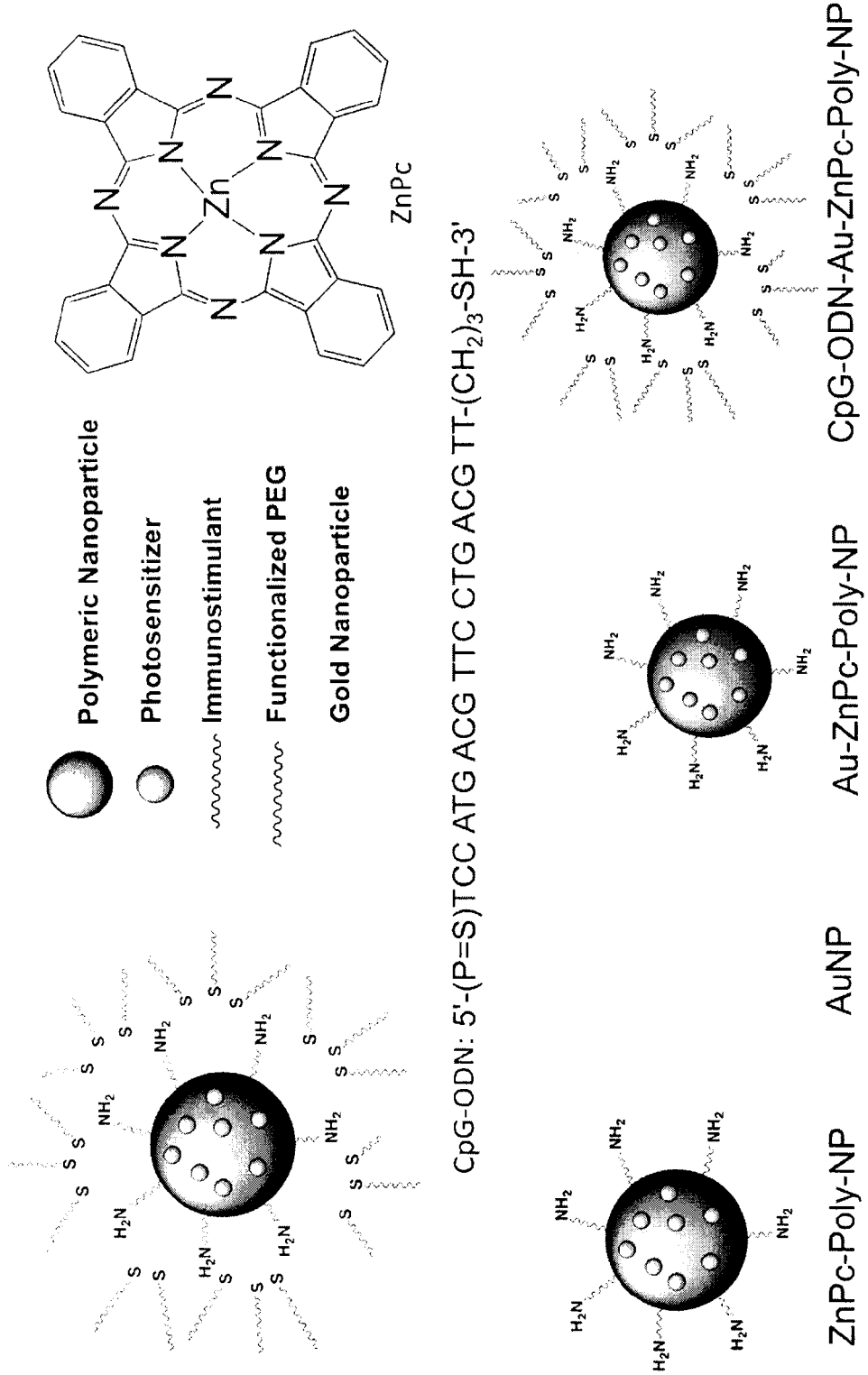
FIGS. 2A and 2B illustrates schematic diagrams of the NP platforms of the disclosure.
Figure 2B:
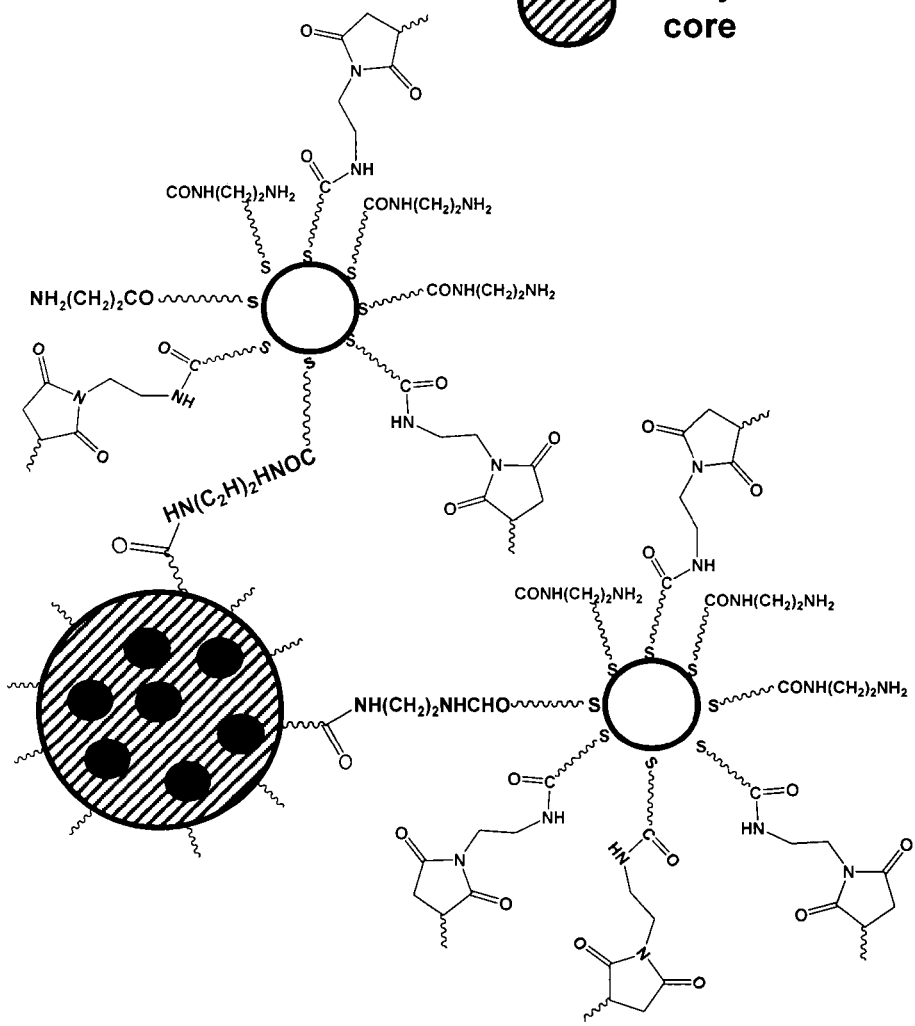
Figure 3:
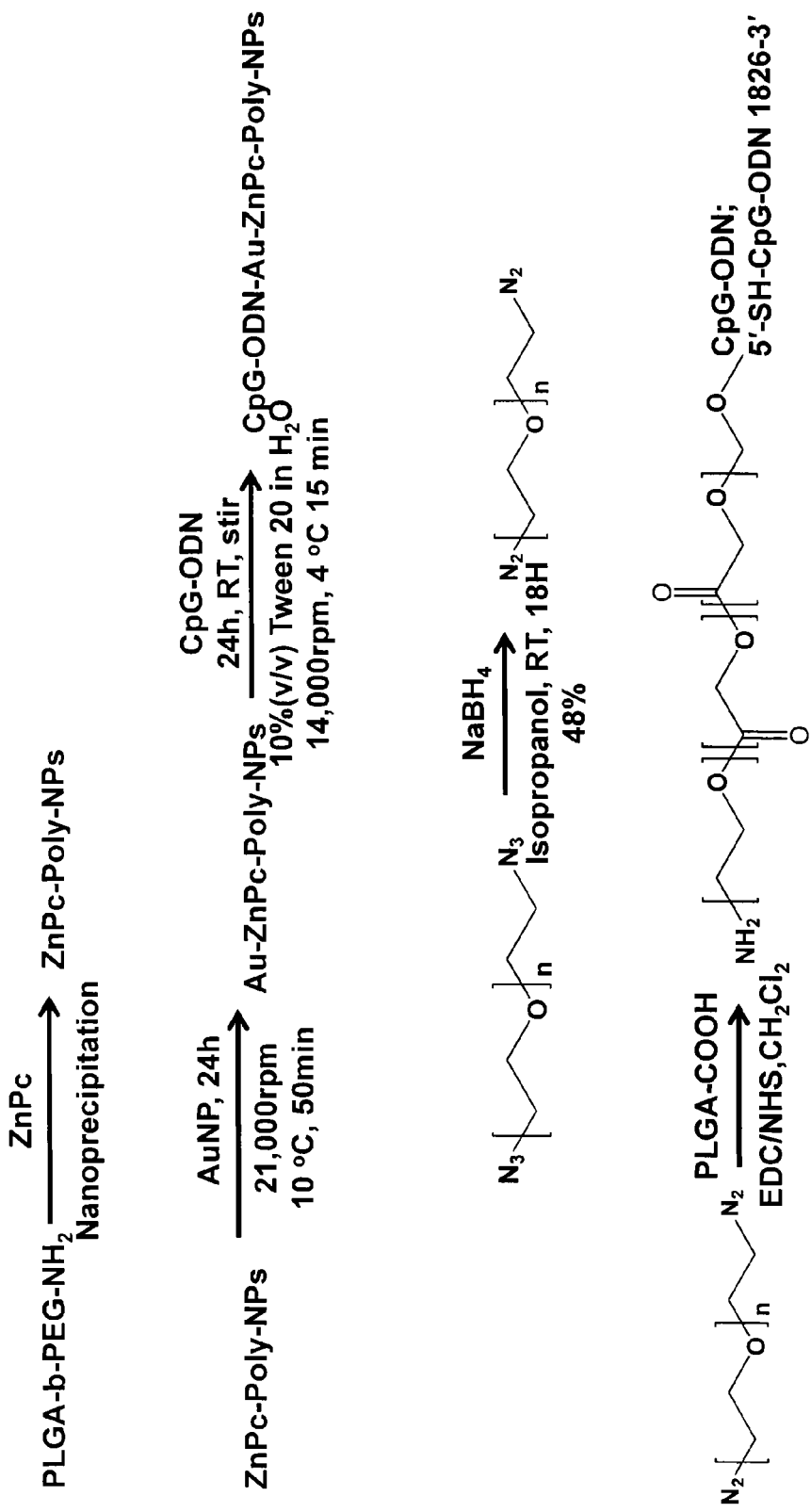
FIG. 3 schematically illustrates a synthetic pathway for the generation f nanoparticles according to the disclosure.

The present disclosure encompasses compositions and methods of their use to differentially deliver a photosensitizer and synergistic immunoadjuvants in a temporally regulated manner. By combining controlled-release nanoparticles (NPs), photodynamic therapy, and immune activation in a single moiety, a potentially safer and more effective management cancer, including but not limited to the deadly forms of metastatic cancer, are possible. The present disclosure, therefore, provides biodegradable hybrid nanoparticle platforms that include a core nanoparticle encapsulating a photosensitizer to which may be attached a plurality of metallic nanoparticles such as, but not limited to gold nanoparticles (AuNP) coated in immunostimulant molecules, as shown schematically in FIGS. 2A and 2B. A synthesis pathway is illustrated in FIG. 3. In the embodiments of the disclosure, it is contemplated that the photosensitizer may be embedded in a polymer nanoparticle wherein the photosensitizer molecules or nanoparticles are dispersed throughout the mass of a polymer, or the photosensitizer may be concentrated in a core and substantially surrounded by a coat or capsule of the polymer. It is further contemplated that the polymer in either case may be hydrated, but most advantageously is biodegradable in the recipient animal or human thereby releasing photosensitizer moieties or reducing the half-life of the hybrid nanoparticles in the recipient subject.

Polymeric nanoparticles of poly(lactide-co-glycolide)-b-polyethyleneglycol (PLGA-b-PEG) block copolymers are especially promising as drug delivery vehicles (Dhar et al., (2008) *Proc. Natl. Acad. Sci. USA* 105: 17356-17361; Dhar et al., (2011) *Proc. Natl. Acad. Sci. USA* 108: 1850-1805; Farokhzad et al., (2004) *Cancer Res.* 2004; Kolishetti et al., (2010) *Proc. Natl. Acad. Sci. USA* 107: 17939-17944; Soppimath, T. M. J (2001) *Controlled Rel,* 70:1-20; Langer (2001) *Science* 293: 58-59). The use of PLGA and PEG polymers in the Food and Drug Administration (FDA) approved products makes these biomaterials ideal for the development of new therapeutics. It is, however, contemplated that other polymers, including block co-polymers may be used in the compositions of the disclosure and in particular if they can be biodegraded after administration to a recipient animal or human subject. For example, but not intended to be limiting, biodegradable polymers suitable for use in the nanoparticles of the disclosure can comprise polymerized monomers, alone or in combination, include such as, but not limited to, (i) polyesters including, for example, poly(glycolic acid), poly(lactic acid), poly(lactic-co-glycolic acid), poly(ε-caprolactone), and poly(phosphoesters). PLGA polymers are cleaved into monomeric acids (i.e., lactic and glycolic acids) that are consequently eliminated from the body as carbon dioxide and water. Poly(ε-caprolactone) (PCL) is a biodegradable, semicrystalline polymer having a low glass transition temperature (about 60° C.). It has the ability to form compatible blends with other polymers. Poly(phosphoesters) (PPEs) have been used recently for delivery of low molecular weight drugs as well as high molecular weight proteins and DNA. This type of polymer degrades under physiological conditions via hydrolysis or enzymatic cleavage if the phosphate bonds in the backbone. Since the chemical structure can be tailored during synthesis, it is possible to obtain PPEs with a wide range of physicochemical properties. The degradation rate of PPEs is controllable by percentage of phosphate content in the backbone, increasing with increasing phosphate content of the polymer; (ii) poly(orthoesters) such as, but not limited to, POE I, POE II, POE III, and POE IV; (iii) polyanhydrides such as the polyanhydride derived from sebacic acid and 1,3-bis(p-carboxyphenoxy) propane, i.e. poly[bis(p-carboxyphenoxy) propane-co-sebacic acid]; (iv) polyphosphazenes such as polydichlorophosphazene (PDPP) reacted with highly reactive phosphorus-chlorine bonds of PDPP with alkoxide, primary (or secondary) amines, and organometallic reagents]. Because there are numerous substituents capable of being introduced into the backbone, a broad spectrum of polyphosphazenes can be synthesized by choosing the type and ratios and appropriate side groups. A few examples, synthesized for biomedical applications, are polyphosphazene-bearing amino acid ester, imidazole, glucosyl amino, glycolic acid ester, and lactic acid ester side groups; and (v) natural polymers such as chitosan, primarily composed of 2-amino-2-deoxy-β-D-glucopyranose (D-glucosamine), and the like.

An exemplary photosensitizer incorporated into the nanoparticles of the disclosure, while not intended to be limiting, is zinc(II) phthalocyanine (ZnPc). This photosensitizer is especially advantageous because of its high optical absorption coefficient in the 600 to 800 nm phototherapeutic window, which is higher than the FDA approved photodynamic therapy drug PHOTOFRIN®. It is contemplated that the photosensitizer can be encapsulated inside the PLGA-b-PEG polymeric nanoparticles, wherein the photosensitizer forms a core substantially surrounded by a layer or coat of the biodegradable polymer. In the alternative, embodiments of the disclosure can comprise a polymeric nanoparticle having photosensitizer molecules or nanoparticles comprising the photosensitizer embedded and therefore dispersed throughout the polymer nanoparticle. In either embodiment, the photosensitizer and the polymer combined form a nanoparticle core. The surface of the nanoparticle core may then modified by attaching thereto a plurality of metallic (gold) nanoparticles (AuNPs) by using non-covalent interactions.

For immune stimulation, the surface of the AuNPs was utilized to introduce 5'-purine-purine/T-CpG-pyrimidine-pyrimidine-3'-oligodeoxynucleotides (CpG-ODN) as a potent dendritic cell activating agent (Yamamoto et al., (2002) *J. Infect. Dis.* 55: 37-44; Weeratna et al., (2005) *Vaccine* 23: 5263-5270). It is, however, contemplated that other CpG-oligonucleotides may be used in the nanoparticles of the disclosure, such as CpG oligodeoxy nucleotides (or CpG ODN) are short single-stranded synthetic DNA molecules that contain a cytosine "C" followed by a guanine "G". The "p" refers to the phosphodiester backbone of DNA, however some ODN have a modified phosphorothioate (PS) backbone. When these CpG motifs are unmethylated, they act as immunostimulants. The CpG PAMP (pathogen-associated molecular pattern) is recognized by the pattern recognition receptor (PRR) Toll-Like Receptor 9 (TLR9), which is constitutively expressed only in B cells and plasmacytoid dendritic cells (pDCs) in humans and other higher primates.[

Synthetic CpG ODN differs from microbial DNA in that it has a partially or completely phosphorothioated (PS) backbone instead of the typical phosphodiester backbone and a poly G tail at the 3' end, 5' end, or both. PS modification protects the ODN from being degraded by nucleases such as DNase in the body and poly G tail enhances cellular uptake. There are five designated classes, Classes A, Class B, Class C, Class P, and Class S.

Class A stimulates the production of large amounts of Type I interferons, the most important one being IFNα, and induced the maturation of pDCs, and are also strong activators of NK cells through indirect cytokine signaling. Structural features defining Class A ODN are: a poly G sequence at the 5' end, the 3' end, or both, an internal palindrome sequence, GC dinucleotides contained within the internal palindrome, and a partially PS-modified backbone Class A oligonucleotides typically contain 7 to 10 PS-modified bases at one or both ends that resist degradation by nucleases and increase the longevity of the ODN. Variability of the sequence is possible. Changes to the sequence can affect the magnitude of the response. For example, the internal palindrome sequence can be 4 to 8 base pairs in length and vary in the order of bases, however the pattern, 5'-Pu Pu CG Pu Py CG Py Py-3', has been found to be the most active when compared to several other sequences. The poly G tail found at either end of the DNA strand can vary in length and even number but its presence is critical to the activity of the molecule.

Class B oligonucleotides are strong stimulators of human B cell and monocyte maturation, the stimulation of the maturation of dendritic cells and result in small amounts of IFNα. Characteristic features of this class are: one or more 6-mer CpG motifs 5'-Pu Py C G Py Pu-3, a fully phosphorothioated (PS-modified) backbone, and typically 18 to 28 nucleotides in length. The strongest ODNs in this class have three timer sequences (Hartmann et al., (2000). *Journal of immunology* 164: 1617-1624) Class B ODNs have been studied extensively as therapeutic agents because of their ability to induce a strong humoral immune response, making them ideal as a vaccine adjuvant.

Immunostimulants (immunoadjuvants) suitable for use in the embodiments of the disclosure include, but are not limited to, the TLR4 agonist monophosphoryl lipid A, CpG (TLR9) and adenosine derivatives thereof, RNA sequences containing poly-U or GU-rich sequences activated by synthetic imidazoquinolines, and guanosine analogues such as LOXORIBINE® that stimulate TLR7/8.

It is further contemplated to be within the scope of the disclosure for embodiments of the hybrid nanoparticles to include a linker moiety for the covalent attachment of the immunostimulant (immunoadjuvant) to the nanoparticle core comprising the photosensitizer.

The main role of the immunoadjuvant is to potentiate the phagocytosis of necrotic or apoptotic tumor cells by already present DCs and to induce DC maturation and migration to draining lymph nodes. The PDT-induced damage will be present for the DCs to take up when stimulated with immunoadjuvant. Accordingly, a covalent construct is contemplated, where immunoadjuvant-decorated AuNPs are covalently linked to the photosensitizer-encapsulated polymeric nanoparticles with photocleavable linkers that can be cleaved at the same wavelength light used to excite the photosensitizer. Photocleavable linkers can have functional groups (herein designated A and B) at either end of a spacer arm, wherein A can be, for example, a dithioorthoformate group serving to alkoxymethylenate carbonyl-bearing groups that are on the surface of polymeric nanoparticles, while B can be a silylprotected hydroxyl that can serve to esterify carboxyl-bearing AuNPs. The linker moiety can be any of a variety of simple alkyl chains, for example, —$(CH_2)_n$— where n is from 1 to about 10, or complex structures like steroids can be used as spacers and selected according to desired pharmacokinetic properties of the conjugates. Thus, in one embodiment that is not intended to be limiting, a linker can be prepared from 1,5-pentandiol. Photo-irradiation of the final conjugate at room temperature using 660 nm light to sensitize the photosensitizer for photodynamic therapy can result in the subsequent release of the AuNP-immunoadjuvant for DC activation.

A therapeutic technology that combined the phototoxic and immune-stimulating ability of photodynamic therapy (PDT) with the widespread effectiveness of the immune system could be useful to treat metastatic breast cancer. Therapeutic challenges when administering therapeutic combinations include the choice of dosages to reduce side effects, the definitive delivery of the correct drug ratio, and exposure to the targets of interest. These factors are difficult to achieve when drugs are individually administered. By combining controlled release polymer-based nanoparticle drug delivery approaches, it was found to be possible to differentially deliver a zinc phthalocyanine (ZnPc) based photosensitizer to metastatic breast cancer cells along with CpG-ODN, a single-stranded DNA that is a known immunostimulants. This allowed management of distant tumors in a temporally regulated manner resulting in more effective management of deadly metastatic breast cancer. In vitro cytotoxicity using 4T1 metastatic mouse breast carcinoma cells showed significant photocytotoxicity of the hybrid nanoparticles containing both ZnPc and CpG-ODN after irradiation with a 660 nm laser light and this activity was synergistically greater than either treatment alone. Treatment of mouse bone marrow-derived dendritic cells with the PDT-killed 4T1 cell lysate showed that the combination of photodynamic therapy with a synergistic immunostimulant in a single NP system results in significant immune response that can be used for the treatment of metastatic cancer.

Figure 4A:
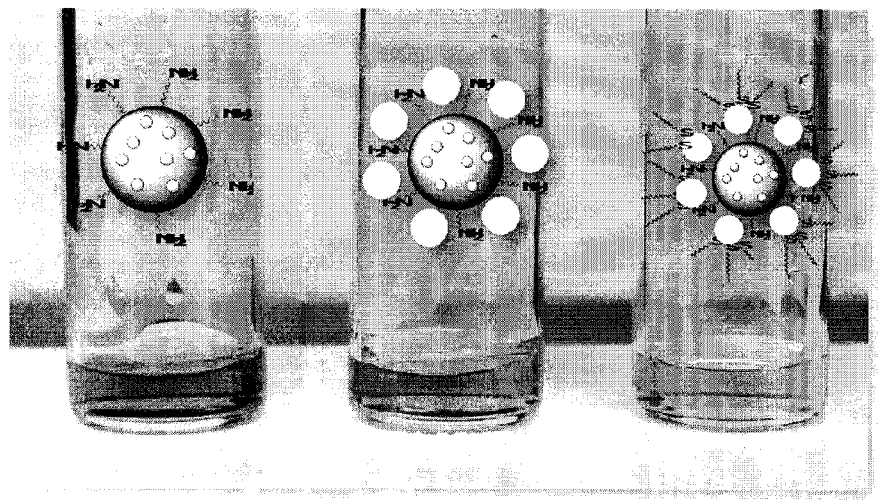
FIGS. 4A-4E illustrate the characterization of hybrid NP constructs.
Figure 4B:
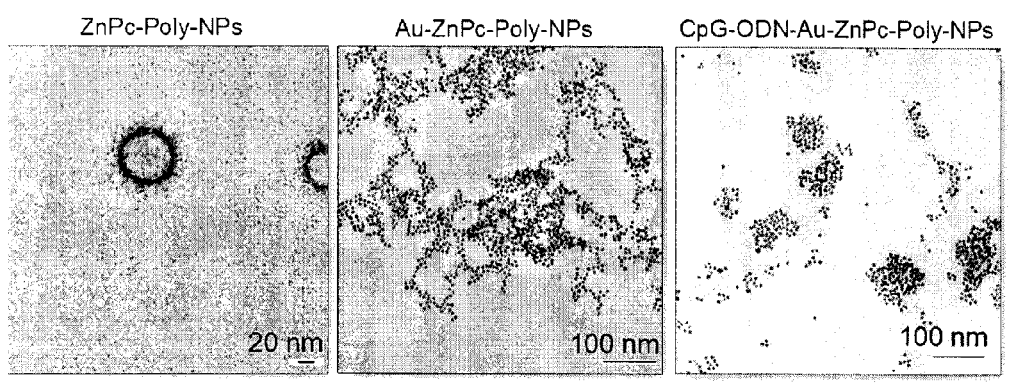
Figure 4C:
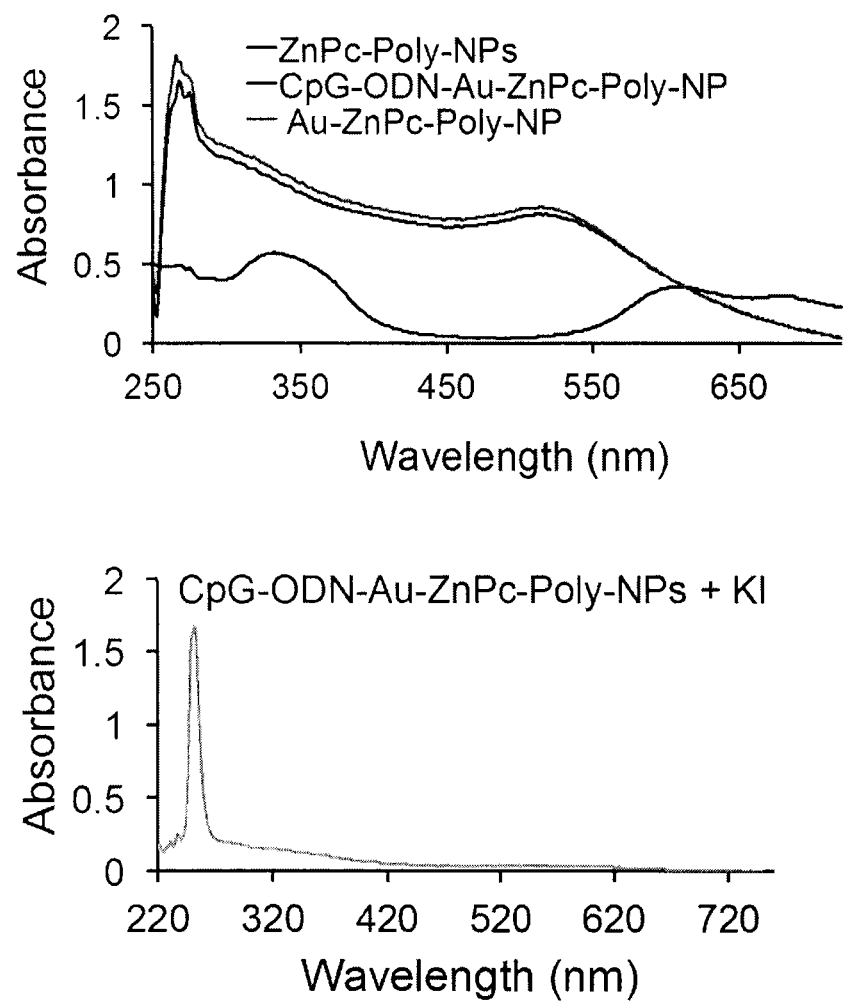

Accordingly, the present disclosure provides embodiments of a hybrid NP to load both photosensitizer and an immunoadjuvant. A hydrophobic photosensitizer is required to achieve high loading inside polymeric nanoparticles. ZnPc, which is hydrophobic provided an example of the required solubility needed for encapsulation inside the hydrophobic core of biodegradable PLGA-b-PEG-$NH_2$ nanoparticles. The terminal $NH_2$ groups were used as handles for coupling of anionic citrate-stabilized AuNPs through non-covalent electrostatic interaction. The formation of the AuNP coated nanoparticles were evident from the changes in the zeta potential and appearance of the surface plasmon band at 520 nm in the absorption spectrum. Addition of ZnPc-Poly-NPs to AuNPs did not cause any visible aggregation (FIG. 4A). This was followed photometrically by observing the decrease and/or red shift of the plasmon absorption band of AuNPs at approximately 520 nm. Absence of any change in the 520 nm band confirms that this hybrid nanoparticle system is stable (FIG. 4C). Formation of the hybrid nanoparticles were also evident from the TEM images (FIG. 4B). This non-covalent attachment approach was used so that ZnPc inside the polymeric core can be released inside the cancer cells, whereas CpG-ODN containing AuNPs will be detached from the polymeric nanoparticles and can be engaged in activating tumor associated DCs after PDT.

The AuNP surface has many advantageous properties such as chemical stability, a highly electron dense core, and ease of conjugation to oligonucleotides. CpG-ODNs are powerful stimulators of innate as well as adaptive immune responses; however, the immunopotency of CpG-ODN is less when given in the free form. The compositions of the disclosure comprising immobilizing CpG-ODN on the AuNP surface for immediate release after photodynamic therapy specifically targets CpG-ODN for uptake by the immune cells. Immobilization of CpG-ODN was confirmed by UV-vis spectroscopy (FIG. 4C).

In CpG-ODN-Au—ZnPc-Poly-NPs, the Au core masks DNA absorption band. The DNA band appears at 260 nm upon dissolution of the Au core by KI and confirms the presence of CpG-ODN in the hybrid nanoparticles (FIG. 4C). A nuclease-resistant phosphorothioate backbone was used, which is known to improve the stability of an optimal CpG-ODN and its ability to activate B cells and DCs, and to induce cytokine production (Krieg et al., (1995) *Nature* 374: 546-549; Hartmann et al., (1999) *Proc. Natl. Acad. Sci. USA* 96: 9305-9310; Krieg et al., (1996) *Antisense Nucleic Acid* 6: 133-139; Liang et al., (1996) *J. Clin. Invest.* 98: 1119-1129). However, it is important to note that the phosphorothioate backbone also reduces the ability to activate natural killer (NK) cells and thus may be less useful for tumor immunotherapy applications that depend on these effector cells.

NP stability in aqueous solution is useful for their utility as a drug delivery vehicle in vivo. NP size is one of the most critical parameters that determine systemic circulation lifetime and NP ability to passively accumulate in tumor tissues and nanoparticles with a size range of 10-150 nm are on demand for systemic drug delivery. Surface zeta potential is also a critical factor to determine both in vitro and in vivo stability of the nanoparticles. An aqueous suspension of 5 mg/mL CpG-ODN-Au—ZnPc-Poly-NPs stored at 4° C. for 1 month did not show observable aggregation (Table 2). Such excellent stability of these nanoparticles renders them suitable for biomedical applications in vivo. However, when NP concentration is too high, there is always a chance of aggregation. Total volume fraction of nanoparticles in the solution, PLGA length, PEG ratio, and PEG surface density can be varied to tune NP stability for possible in vivo applications.

Figure 5A:
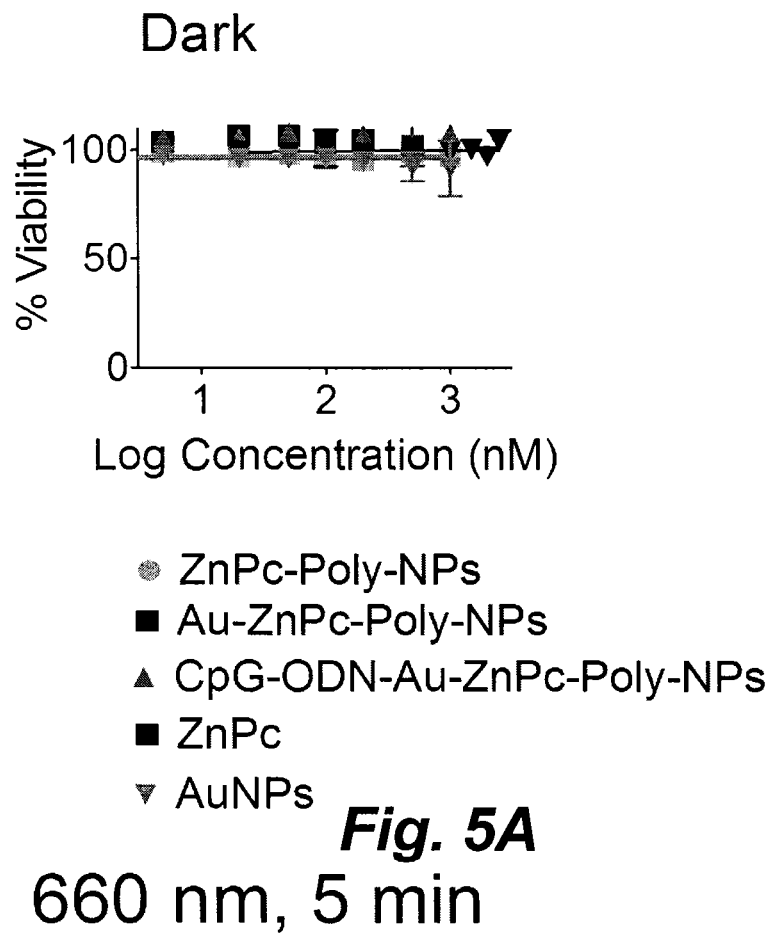
FIG. 5A is a graph illustrating the cytotoxicity profiles of ZnPc-Poly-NPs, Au—ZnPc-Poly-NPs, and CpG-ODN-Au—ZnPc-Poly-NPs in 4T1 cells in the dark. Free ZnPc and AuNPs were used as controls.
Figure 5B:
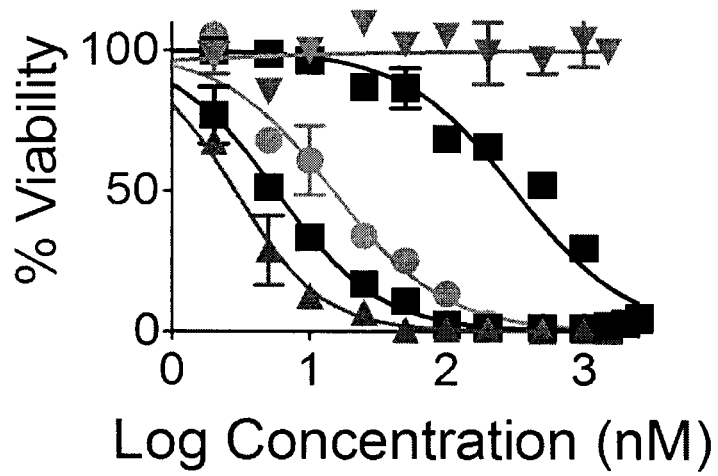
FIG. 5B is a graph illustrating the cytotoxicity profiles of ZnPc-Poly-NPs, Au—ZnPc-Poly-NPs, and CpG-ODN-Au—ZnPc-Poly-NPs in 4T1 cells after 5 min exposure with a 660 nm LASER. Free ZnPc and AuNPs were used as controls.

A mouse mammary tumor cell line 4T1, one of only a few breast cancer models with the capacity to metastasize, was used to test the in vitro photodynamic activity and photodynamic therapy mediated anti-tumor immunity with our construct. It is poorly immunogenic, spontaneously metastatic, and highly malignant. A series of in vitro cytotoxicity assays was carried out to evaluate the potential of our engineered hybrid NP construct containing both ZnPc and CpG-ODN in metastatic breast cancer using 4T1 cells and directly comparing its efficacy to that of free ZnPc, AuNPs, ZnPc-Poly-NPs, and Au—ZnPc-Poly-NPs. As represented in FIG. 5B, CpG-ODN-Au—ZnPc-Poly-NPs are highly phototoxic to 4T1 cells, having an $IC_{50}$ value of 2.8 nM when irradiated with a 660 nm laser for only 5 min. This construct has no toxicity in the dark (FIG. 5A). Under similar conditions, nanoparticles containing the photosensitizer alone (ZnPc-Poly-NPs) have an $IC_{50}$ value of 15 nM, and for free ZnPc the value with these cells is 317 nM, approximately 2 orders of magnitude less effective. Significant phototoxicity of our construct is indicative of the potential of a synergistic combination of a photosensitizer and an immuoadjuvant in a single delivery platform to treat metastatic breast cancer.

CpG-ODN stimulates B cells, NK cells, DCs, and macrophages, regardless of whether the DNA is in the form of genomic bacterial DNA or in the form of synthetic ODN. The production of high-affinity antibodies and the gene ration of cytotoxic T cells that provide long-lasting protection characterize the resultant antigen-specific immunity during photodynamic therapy. The use of CpG-ODN in combination with ZnPc in a single NP construct had a significant immune response after PDT. TLR9 recognizes d(CpG) dinucleotides present in the synthetic CpG-ODN used in our construct. CpG-ODN has strong immunostimulatory activity on murine and human immune cells in vitro and in vivo, such as: induction of tumor specific Th17 response, triggering B cell proliferation, NK cell secretion of IFN-γ, increased lytic activity, and macrophage secretion of IFN-α/β, IL-6, IL-12, granulocyte-monocyte colony-stimulating factor, chemokines, and TNF-α. One important question to answer in designing any combinatory therapy is the order of administration of the respective component treatments, their local concentration, and the stoichiometric ratio. These parameters are very difficult to control when the components are administered separately.

The hybrid NP systems of the present provide photodynamic therapy first followed by release of CpG-ODN for further enhancement of PDT-mediated antitumor immunity. The chief role of CpG-ODN is to potentiate phagocytosis of necrotic or apoptotic tumor cells by already present DCs and to induce DC maturation and migration to draining lymph nodes. CpG-ODN activation after photodynamic therapy will be superior since the photodynamic therapy-induced damage will further enhance over all DC activity when stimulated with CpG-ODN conjugate. The results showed that the combination of ZnPc and CpG-ODN in a single nanoparticle construct was significantly better than either treatment alone. Treatment of DCs with photodynamic therapy-cell lysates and CpG-ODN from a controlled-release nanoparticle could produce improved systemic immune responses due to the creation of potential tumor antigenic fragments before the immune stimulation, which facilitates uptake of antigen presenting cells. The immunosuppressive tumor environment is one of the key players of compromised anti-tumor immune responses. The dominant immunosuppressive cytokines in the tumor microenvironment are IL-10, transforming growth factor, and vascular endothelial growth factor, which inhibit DC maturation/activation.

Figure 6A:
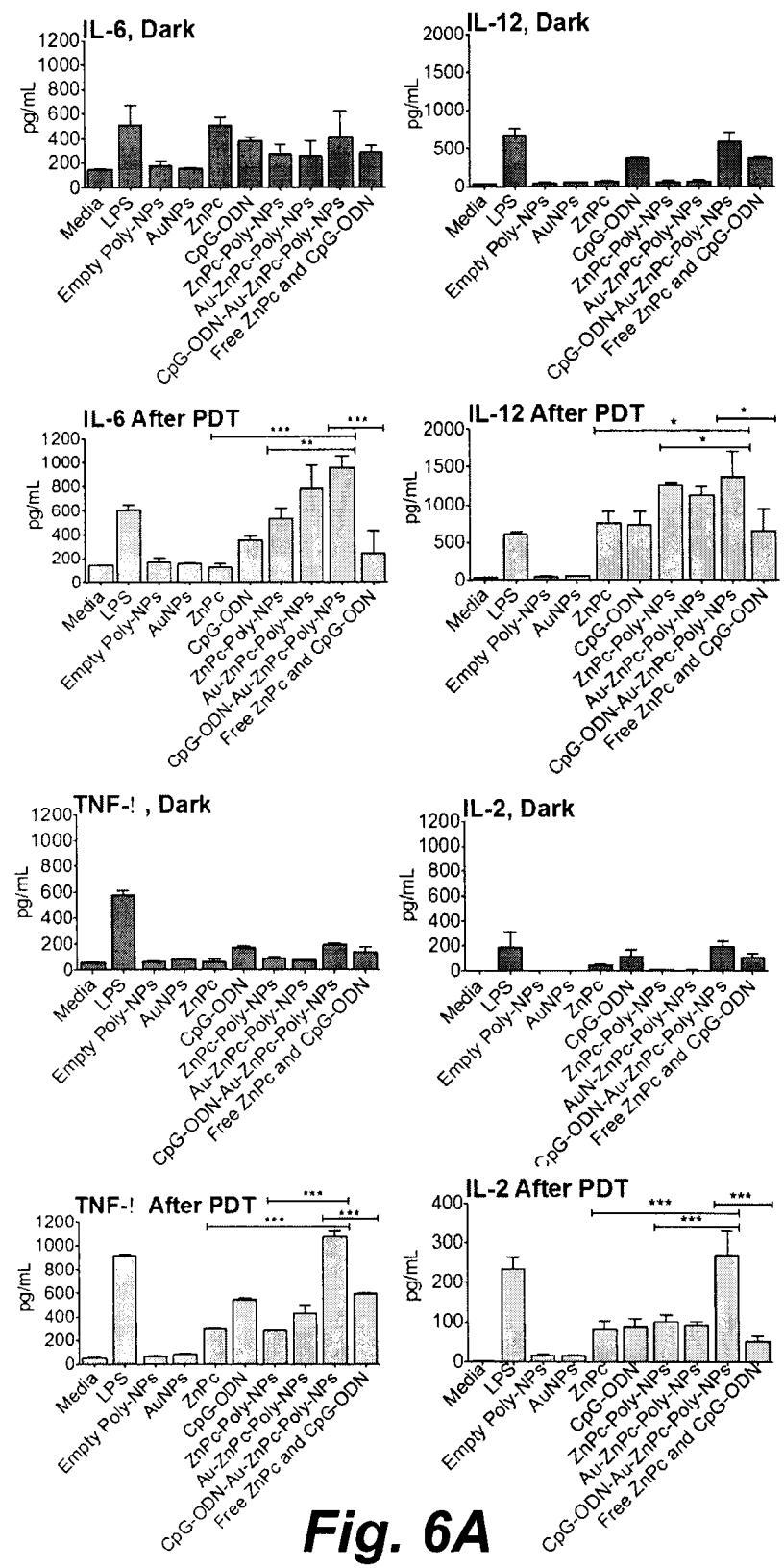
FIGS. 6A and 6B illustrate a series of bar graphs illustrating that a combination of ZnPc and CpG-ODN in a single NP construct potentiate immune responses after PDT. Asterisks indicate significant differences between CpG-ODN-Au—ZnPc-Poly-NPs, ZnPc-Poly-NPs, free ZnPc, and a 1:1 combination of free ZnPc and CpG-ODN according to one-way ANOVA with Tukey post hoc test. Single, double, and triple asterisks indicate a P value <0.05, <0.004, and <0.001, respectively.
Figure 6B:
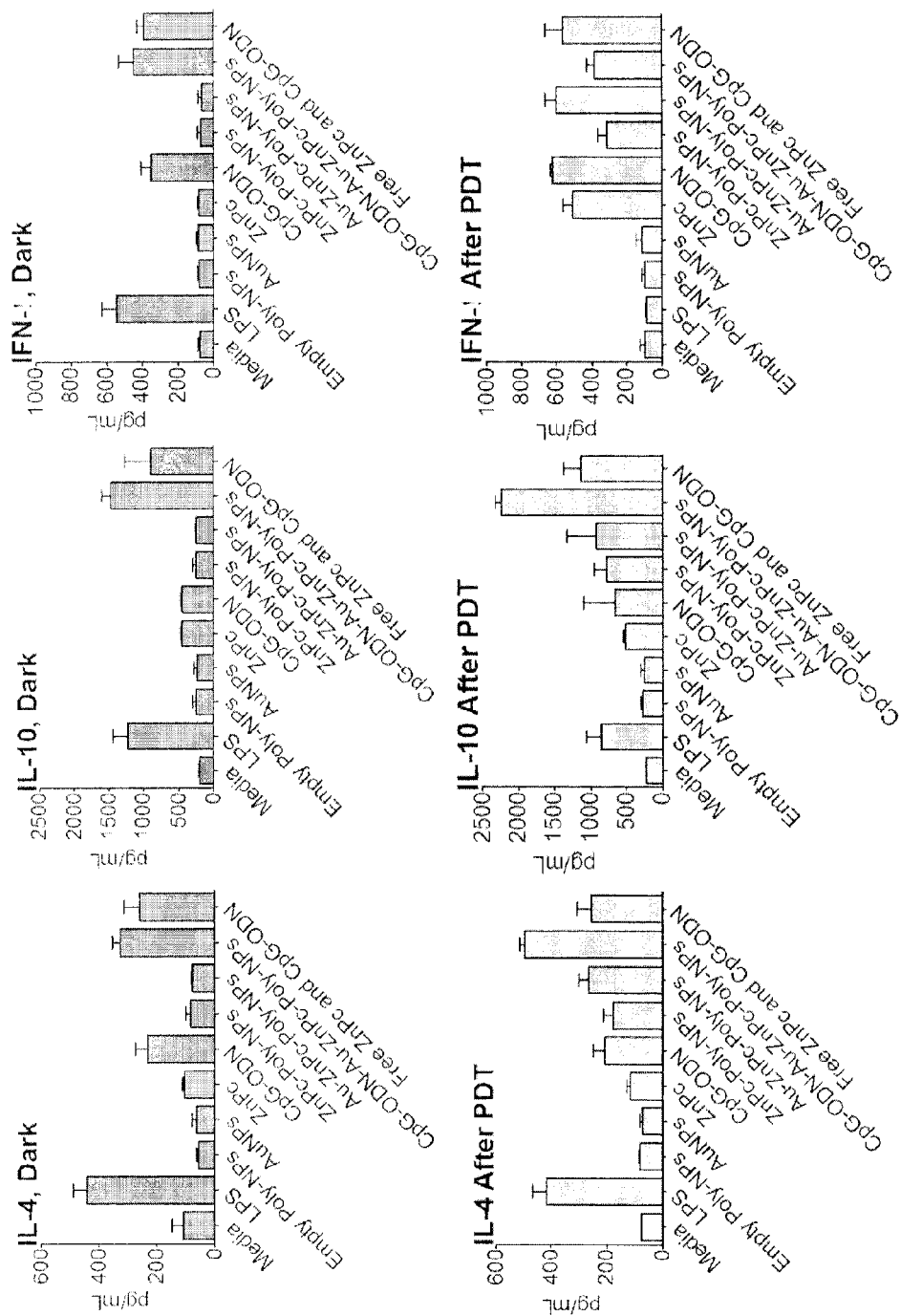

One of the most remarkable finding of the current study is the ability of the hybrid nanoparticle formulation to shift the balance at the tumor microenvironment towards immune stimulation, as evidenced by the increase in the level of proinflammatory/Th1-biased cytokines IL-2, IL-6, IL-12, TNF-α and minimal effect in the level of the immunosuppressant such as IL-10 (FIGS. 6A and 6B). A hybrid NP-based delivery of photodynamic therapy and CpG-ODN can produce effective synergistic response by activating innate and adaptive antitumor immunity, which can be used as a more effective adjuvant for tumor vaccines as well as immunotherapeutic adjuvant.

One aspect of the disclosure encompasses embodiments of a multifunctional hybrid nanoparticle, the hybrid nanoparticle comprising: a nanoparticle core comprising a photosensitizer and a polymer; a plurality of metallic nanoparticles disposed on the surface of the nanoparticle core; and an immunostimulant disposed on the plurality of metallic nanoparticles.

In embodiments of this aspect of the disclosure, the photosensitizer can produce an activated oxygen species when irradiated with a light energy.

In embodiments of this aspect of the disclosure, the photosensitizer can be selected from the group consisting of: a porphyrin, a chlorophyll, a dye, a metallosensitizer, a quantum dot, or any combination thereof.

In embodiments of this aspect of the disclosure, the photosensitizer can be selected from the group consisting of: aminolevulinic acid (ALA), silicon phthalocyanine Pc 4, m-tetrahydroxyphenylchlorin (mTHPC), mono-L-aspartyl chlorin e6 (NPe6), tris-(2,3-naphthalocyanato)bis-chloro-aluminium(III), tris-(2,3-naphthalocyanato)bis-chlorozinc (II), and (zinc(II) phthalocyanin (ZnPc)).

In embodiments of this aspect of the disclosure, the polymer of the nanoparticle core can be biodegradable, and wherein the photosensitizer is embedded in the polymer or the photosensitizer is encapsulated by the polymer, or disposed on the surface of a polymer nanoparticle.

In some embodiments of this aspect of the disclosure, the nanoparticle core can comprise a polymer of poly (D,L-lactic-co-glycolic acid)-b-poly(ethylene glycol), and can further comprise a plurality of functional groups exposed at the surface of the nanoparticle core and capable of receiving the metallic nanoparticles thereon. In these embodiments, the functional groups exposed at the surface of the nanoparticle core and capable of receiving the metallic nanoparticles thereon can comprise PEG-amine moieties extending from the surface of the nanoparticle core.

In embodiments of this aspect of the disclosure, the metallic nanoparticles can be gold nanoparticles, silver nanoparticles, copper nanoparticles, nickel nanoparticles, ferrous nanoparticles, or any combination thereof.

In some embodiments of this aspect of the disclosure, the metallic nanoparticles are gold nanoparticles.

In embodiments of this aspect of the disclosure, the immunostimulant disposed on the metallic nanoparticles can be selected from the group consisting of: a CpG-ODN, aTLR4 agonist monophosphoryl lipid A, a CpG (TLR9) or adenosine derivative thereof, an RNA comprising a poly-U or GU-rich sequence, an imidazoquinoline, and a guanosine analog ues that stimulates TLR7/8.

In embodiments of this aspect of the disclosure, the immunostimulant can be disposed on the metallic nanoparticles non-covalently.

In embodiments of this aspect of the disclosure, the immunostimulant is disposed on the metallic nanoparticles covalently.

In embodiments of this aspect of the disclosure, the immunostimulant is disposed on the metallic nanoparticles by a linker moiety.

In embodiments of this aspect of the disclosure, the linker moiety is cleavable, thereby releasing the immunostimulant from the multifunctional hybrid nanoparticle.

In embodiments of this aspect of the disclosure, the CpG-ODN comprises a phosphorothioate backbone.

In some embodiments of this aspect of the disclosure, the photosensitizer is zinc pthalocyanine, the nanoparticle core comprises a biodegradable polymer of poly (D,L-lactic-co-glycolic acid)-b-poly(ethylene glycol), the metallic nanoparticles are gold nanoparticles, and the immunostimulant disposed on the metallic nanoparticles is a CpG-ODN.

Another aspect of the disclosure encompasses embodiments of a method of reducing the viability of a cell comprising the steps of: (i) administering to an animal or human subject a pharmaceutically acceptable composition comprising a multifunctional hybrid nanoparticle comprising a nanoparticle core comprising a photosensitizer and a polymer, a plurality of metallic nanoparticles disposed on the surface of the nanoparticle core; and an immunostimulant disposed on the metallic nanoparticles, and where the immunostimulant generates an immune response in the animal or human subject that reduces the viability of a cell or population of cells in the subject; and (ii) irradiating the cell with a light energy having a wavelength generating a photoactivated species by the photosensitizer.

In embodiments of this aspect of the disclosure, the photosensitizer is zinc pthalocyanine, the nanoparticle core comprises a biodegradable poly mer of poly (D,L-lactic-co-glycolic acid)-b-poly(ethylene glycol), the metallic nanoparticles are gold nanoparticles, and the immunostimulant disposed on the metallic nanoparticles is a CpG-ODN, wherein the photosensitizer produces activated oxygen species.

In embodiments of this aspect of the disclosure, the cell or population of cells is a cancerous cell or a tumor.

Yet another aspect of the disclosure encompasses embodiments of a pharmaceutically acceptable composition comprising a multifunctional hybrid nanoparticle comprising a nanoparticle core comprising a photosensitizer and a polymer; a plurality of a metallic nanoparticle disposed on the surface of the nanoparticle core; and an immunostimulant disposed on the surfaces of the plurality of metallic nanoparticles; and a pharmaceutically acceptable carrier.

In some embodiments of this aspect of the disclosure, the photosensitizer can be zinc pthalocyanine, the nanoparticle core can comprise a biodegradable polymer of poly (D,L-lactic-co-glycolic acid)-b-poly(ethylene glycol), the metallic nanoparticles are gold nanoparticles, and the immunostimulant disposed on the metallic nanoparticles is a CpG-ODN, where the photosensitizer produces activated oxygen species.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Materials and Methods: All chemicals were used without further purification unless otherwise noted. PLGA-COOH of inherent viscosity of 0.18 dL/g was purchased from Lactel. $NH_2$—PEG-$NH_2$ (MW 2000) was obtained from JenKem USA. 4-dimethylaminopyridine (DMAP), N,N'-dicyclohexylcarbodiimide (DCC), and 3-(4,5-dimethylthiazol-2-yl)-2,5-diphenyltetrazolium bromide (MTT) were purchased from Sigma-Aldrich. AuNPs of size 5 nm ($5 \times 10^{13}$ particles/mL) were purchased from BBInternational. Phosphorothioate oligonucleotide CpG-ODN-1826 of sequence 5'-TCCAT-GACGTTCCTGACGTT-3' (SEQ ID NO.: 1) was purchased from Midland certified reagent company (Midland, Tex.). Granulocyte-macrophage colony-stimulating factor (GM-CSF) was purchased from R&D systems. Cytokines were tested using BD OptEIA mouse enzyme-linked immunosorbent assay (ELISA) kits. Distilled water was purified by passage through a Millipore Milli-Q Biocel water purification system (18.2 MO) containing a 0.22 μm filter. Dynamic light scattering (DLS) measurements for size, zeta potential, and polydispersity index (PDI) were carried out using a Malvern Zetasizer Nano ZS system. $^1$H and $^{13}$C NMR spectra were recorded on a 400 MHz Varian NMR spectrometer. Gel permeation chromatographic (GPC) analyses were performed on Shimadzu LC20-AD prominence liquid chromatographer equipped with a RI detector. Molecular weights were calculated using a conventional calibration curve constructed from narrow polystyrene standards. Optical measurements were carried out on a NanoDrop 2000 spectrophotometer. HPLC analyses were made on an Agilent 1200 series instrument equipped with a multi-wavelength UV-visible detector. Transmission electron microscopy (TEM) images were taken in a FEI Tecnai 20 TEM microscope. LASER irradiation was performed using a Melles Griot 660 nm 56 ICS series diode laser equipped with a fiber optic cable in a dark environment.

Example 2

Cell Line and Cell Culture: The BALB/c mammary adenocarcinoma 410.4_4T1 cells from the American Type Culture Collection (ATCC) were grown in RPMI 1640 media containing HEPES, glutamine, sodium pyruvate, 10% fetal bovine serum (FBS), 100 U/mL penicillin, and 100 μg/mL streptomycin at 37° C. in 5% $CO_2$. Cells were passed every 3 days and restarted from the frozen stocks upon reaching passage number 20.

Example 3

Synthesis of PLGA-b-PEG-$NH_2$: PLGA-b-PEG-$NH_2$ was synthesized by using an amide coupling reaction. $NH_2$-PEG- NH$_2$ (0.7 g, 0.35 mmol), PLGA-COOH (0.8 g, 0.12 mmol), and DMAP (0.16 g, 1.32 mmol) in 10 mL dry CH$_2$Cl$_2$ was set to stir on ice. DCC (34.1 mg, 0.17 mmol) in 1 mL dry CH$_2$Cl$_2$ was added drop wise to the solution. The solution was warmed to room temperature and stirred overnight. It was then filtered to remove the dicyclohexylurea byproduct, precipitated using a mixture of 50:50 methanol-diethyl ether, isolated via centrifugation (5000 rpm, 4° C., 10 min), and lyophilized overnight. PLGA-b-PEG-NH$_2$ was isolated as a white solid in 29% yield. $^1$H NMR(CHCl$_3$-d): δ 5.3 [m, (OCHCH$_3$C(O)], 4.9 [m, (OCH$_2$C(O))], 3.6 [s, (OCH$_2$CH$_2$)], 1.9 [m, (CH$_3$CH)]. $^{13}$C NMR(CHCl$_3$-d): δ 169.6, 166.5, 66.0, 61.1, 60.9, 16.9, 15.5. GPC: Mn=7,070 g/mol, Mw=8,540 g/mol, PDI=1.21.

Example 4

Synthesis of ZnPc-Poly-NPs: ZnPc-encapsulated nanoparticles (ZnPc-Poly-NPs) were prepared by using the nanoprecipitation method. 10b PLGA-b-PEG-NH$_2$ (50 mg/mL) and ZnPc, at varying percent weight with respect to the polymer weight, were dissolved in DMF. This mixture was slowly added to water over a period of 10 min. The nanoparticles formed were stirred at room temperature for 2-3 h and washed 3 times with nanopure water using Amicon ultracentrifugation filtration membranes with a molecular weight cutoff of 100 kDa (3000 rpm, 4° C.). The NP size, PDI, and zeta potential were obtained by DLS measurements. Size and the morphology of the nanoparticles were further confirmed by TEM. The ZnPc content in the nanoparticles was measured by HPLC.

Example 5

Synthesis of Au—ZnPc-Poly-NPs: An aqueous suspension of 1 mL ZnPc-Poly-NPs was added to a 2 mL aqueous solution of citrate coated AuNPs of size 5 nm and allowed to sit for 4 h at room temperature. The nanoparticles were characterized by DLS, TEM, and UV-Vis spectroscopy.

Example 6

Synthesis of CpG-ODN-Au—ZnPc-Poly-NPs: CpG-ODN of sequence 5'-TCCATGACGTTCCTGACGTT-3' (SEQ ID No.: 1) with a disulfide bond in the 5' end was deprotected according to the manufacturer's protocol. Briefly, to a solution of CpG-ODN in 0.1 M triethylammonium acetate buffer (pH 6.5), an aqueous solution of 0.1 M DTT was added and incubated at room temperature for 30 min. The deprotected CpG-ODN was purified using a 50 mg C$^{18}$ Sep-Pak cartridge (Waters, Milford, Mass.) equilibrated in and eluted with DNase/RNase-free distilled water. The concentration of the CpG-ODN was measured by UV-Vis spectroscopy. Au—ZnPc-Poly-NPs were added to an equivalent volume of 10% (v/v) Tween 20 at room temperature. Then CpG-ODN was added (210 μL, 105 μg/mL) and incubated at room temperature in a shaker for 20 h. CpG-ODN-Au—ZnPc-Poly-NPs were washed 3 times using Amicon ultracentrifugation filtration membranes with a molecular weight cutoff of 100 kDa (3000 rpm, 4° C.). Finally, nanoparticles were resuspended in water and analyzed by DLS. NP solutions were analyzed by UV-Vis after dissolving the polymeric core using 1 M NaOH for determination of encapsulated ZnPc content or dissolving the gold core with 0.6 M KI for quantification of conjugated CpG-ODN.

Example 7

Determination of ZnPc Loading and Encapsulation Efficiency: ZnPc loading and encapsulation efficiency (EE) were calculated by dissolving the polymer core by mixing equal portions of the NP solution and 1N NaOH, followed by dilution with a 50:50 water:acetonitrile mixture, and subsequent HPLC analysis (wavelength: 670 nm). ZnPc loading is defined as the mass fraction of photosensitizer in the nanoparticles, whereas EE is the fraction of initial photosensitizer used for encapsulation by the nanoparticles during nanoprecipitation.

Example 8

MTT Assay: The phototoxic behavior of all the nanoparticles was evaluated using the MTT assay against 4T1 cells. 4T1 cells (1500 cells/well) were seeded on a 96-well plate in 100 μL of RPMI medium and incubated for 24 h. The cells were treated with nanoparticles at varying concentrations (with respect to ZnPc) and incubated for 2 h at 37° C. The cells were then irradiated with a 660 nm LASER (power 20 mV) with a fiber optics for 5 min per well. Irradiated cells were incubated for 12 h at 37° C., medium was changed after 12 h, and the cells were incubated for additional 60 h. The cells were then treated with 20 μL of MTT (5 mg/mL in PBS) for 5 h. The medium was removed, the cells were lysed with 100 μL of DMSO, and the absorbance of the purple formazan was recorded at 550 nm using a Bio-Tek Synergy HT microplate reader. Each well was performed in triplicate. All experiments were repeated three times. Cytotoxicity was expressed as mean percentage increase relative to the unexposed control±SD. Control values were set at 0% cytotoxicity or 100% cell viability. Cytotoxicity data (where appropriate) was fitted to a sigmoidal curve and a three parameters logistic model was used to calculate the IC$_{50}$, which is the concentration of the agent causing 50% inhibition in comparison to untreated controls. The mean IC$_{50}$ is the concentration of agent that reduces cell growth by 50% under the experimental conditions and is the average from at least three independent measurements that were reproducible and statistically significant. The IC$_{50}$ values are reported at ±95% confidence intervals (±95% CI). This analysis was performed with Graph Pad Prism (San Diego, U.S.A) software.

Example 9

Generation of Bone Marrow Derived Dendritic Cells: Bone marrow derived dendritic cells (BMDCs) were isolated from 6-8 weeks old C57BL/6 mice. Mice were euthanized and bone marrows were isolated by flushing mouse femurs in RPMI. The harvested cells were centrifuged at 1250 rpm for 10 min and the resulting pellet was resuspended in ice-cold buffer (2 mL) to lyse erythrocytes. The cells were counted, resuspended, and transferred to petri dishes at the final concentration of 1.5×10$^6$ cells/mL. To this culture GM-CSF at 20 ng/mL was added to generate BMDCs. Media was changed on days 2, 4 and 6 and cells were used on day 7.

Example 10

Preparation of PDT Treated 4T1 Cells: 4T1 cells were plated at the concentration of 4×10$^5$ cells/well in six well plates and allowed to grow for 24 h. On the next day, the cells were incubated with 10 nM ZnPc, 6.16 nM CpG-ODN, a mixture of 10 nM ZnPc and 6.16 nM CpG-ODN, 10 nM ZnPc-Poly-NPs, 10 nM Au—ZnPc-Poly-NPs, 10 nM CpG-ODN-Au—ZnPc-Poly-NPs for 2 h, and irradiated with a 660 nm LASER light for 5 min. Cells were left in the culture for 12 h at 37° C. and photodynamic therapy lysates were used for stimulation of the BMDCs.

Example 11

Stimulation of BMDCs with Supernatants from PDT Treated Tumor Cells: The photodynamic therapy lysates obtained 24 h post photodynamic therapy treatment of 4T1 cells were added to freshly prepared BMDCs. Additionally lipopolysaccharide (LPS) alone (100 ng/mL) or CpG-ODN alone (1 µg/mL or 10 µg/mL) was added to the DC cultures as controls. DCs were incubated with the supernatants for 12 h at 37° C. and the supernatants were harvested for further studies.

Example 12

Immune Response by ELISA: ELISA was performed using the supernatants harvested from BMDC culture to measure the levels of cytokines IL-2, IL-4, IL-6, IL-10, IL-12, TNF-α, and IFN-γ according to manufactures protocol. Briefly, the cell supernatants were incubated with antibody-coated plates for 2 h at room temperature. This was immediately followed by washings and sequential incubations with the biotin-conjugated detection antibody and streptavidin-horseradish peroxidase (HRP) solution. Finally, the ELISA was developed by adding the substrate (100 µL/well) to each well followed by a stop solution. The absorbance was recorded at 450 nm using a BioTek Synergy HT well plate reader.

Example 13

Figure 7:
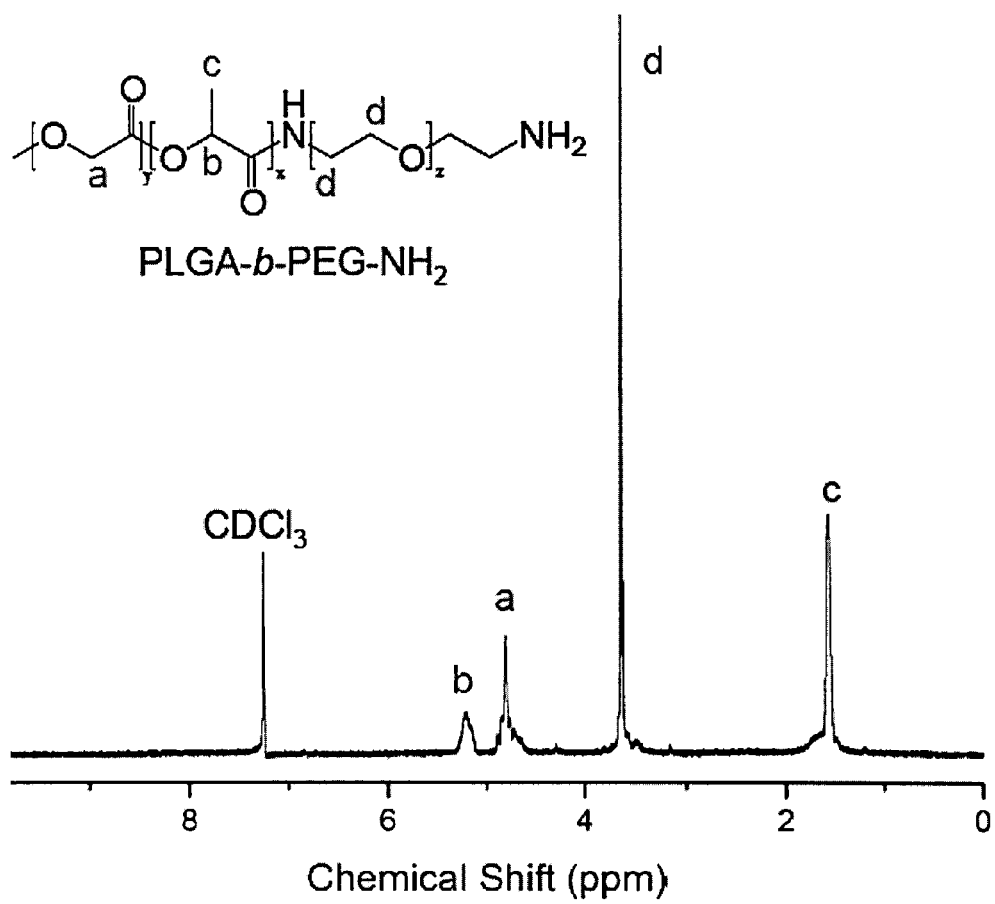
FIG. 7 shows a 1H NMR spectrum of PLGA-b-PEG-NH$_2$ in CDCl$_3$
Figure 8:
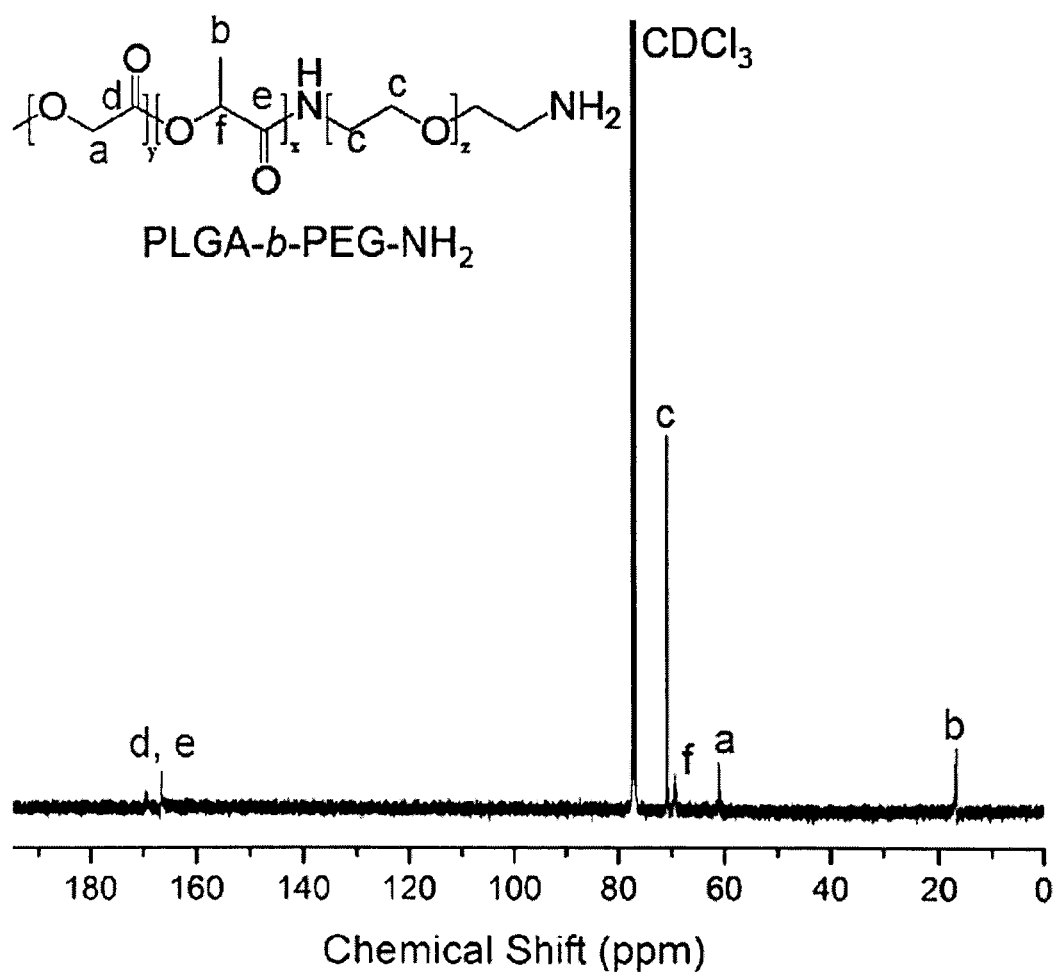
FIG. 8 shows a 13C NMR spectrum of PLGA-b-PEG-NH$_2$ in CDCl$_3$

Synthesis of the Polymer and Construction of the Nanoparticles: To co-deliver photosensitizer and an immunoadjuvant using a single NP construct and to obtain adequate control over encapsulation of the hydrophobic PS, ZnPc, a biodegradable polymer was synthesized with a terminal —$NH_2$ group (PLGA-b-PEG-NH2) via an amide coupling of PLGA-COON with $NH_2$—PEG-$NH_2$ using DCC/DMAP as coupling agents. This polymer was characterized by $^1$H and $^{13}$C NMR spectroscopy, as shown in FIGS. 7 and 8. Purity, molecular weights, and PDI of the polymer were determined by GPC measurements using tetrahydrofuran mobile phase, as shown in Table 1.

TABLE 1

Comparison of molecular weights of PLGA—COOH and PLGA-b-PEH—$NH_2$ as determined from gel permeation chromatographic (GPC) analyses using THF mobile phase and a calibration curve constructed from narrow polystyrene standards at 40° C.

| Molecular weight | PLGA-b-PEG—$NH_2$ | PLGA—COOH |
|---|---|---|
| MW | 8,540 g/mol | 6,750 g/mol |
| Mn | 7,070 g/mol | 4,300 g/mol |
| PDI | 1.21 | 1.57 |

These results are consistent with previously reported data for PLGA-b-PEG-COOH polymer (Gu et al., (2008) *Proc. Natl. Acad. Sci. USA* 105: 2586-2591).

Synthesis of the nanoparticles with PLGA-b-PEG-$NH_2$ was achieved by the nanoprecipitation method, as described in (Dhar et al., (2008) *Proc. Natl. Acad. Sci. USA* 105: 17356-17361; Dhar et al., (2011) *Proc. Natl. Acad. Sci. USA* 108: 1850-1805; Farokhzad et al., (2004) *Cancer Res.* 2004; Kolishetti et al., (2010) *Proc. Natl. Acad. Sci. USA* 107: 17939-17944; Soppimath, T. M. J (2001) *Controlled Rel.* 70. 1-20: Langer (2001) *Science* 293: 58-59; incorporated herein in their entireties).

PLGA-b-PEG-$NH_2$ was dissolved in a water miscible solvent DMF and then added drop wise into an aqueous solution, generating nanoparticles. The properties of the encapsulated nanoparticles were characterized by DLS to give the hydrodynamic diameter, zeta potential, and PDI of each preparation. To optimize the size and loading, a series of encapsulated nanoparticles were prepared by varying the weight percentage of ZnPc to polymer (% w/w) and by using PEG of various molecular masses. When the DMF solution of the polymer and ZnPc was added to water, the mixture became turbid, indicating the formation of nanoparticles. However, depending on the conditions, the final suspension contained a larger or smaller amount of larger polymeric aggregates either dispersed in the aqueous phase or adhering to the flask wall or to the magnetic stirring bar. PLGA of inherent viscosity 0.18 dL/g in hexafluoroisopropanol were found to afford the most suitable encapsulated nanoparticles.

Figures 4D, 4E:
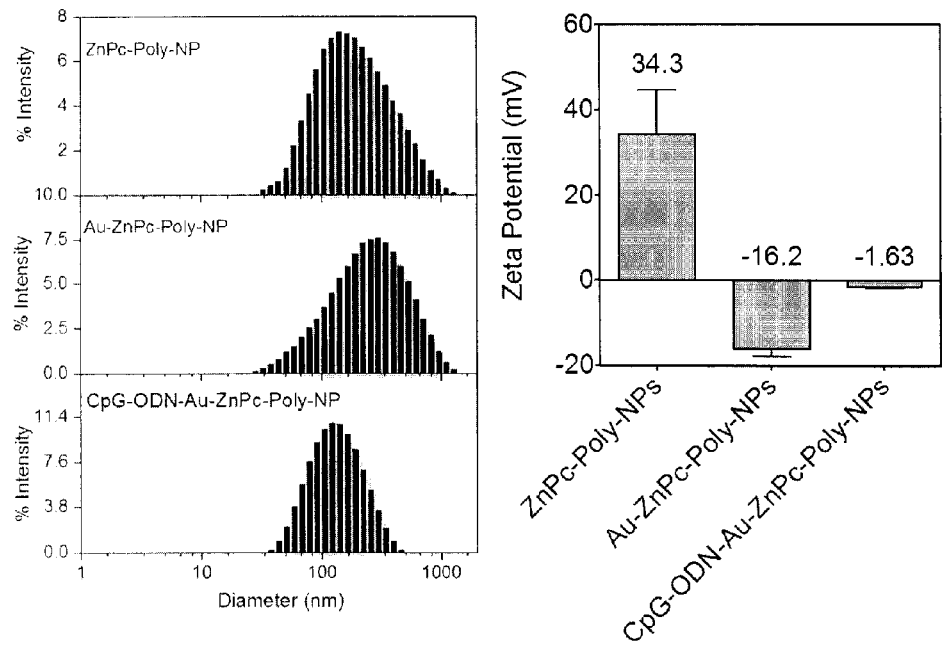

Measurements of nanoparticle size made on three different batches produced under identical conditions had a size variation of about 10%. The loading efficiencies of ZnPc at various added weight percentage with respect to the polymer weight are shown in FIG. 4E. The size of the nanoparticles increased with ZnPc loading (FIG. 4E). For all in vitro studies, encapsulated nanoparticles were used containing 30% ZnPc added with respect to the polymer.

For the synthesis of the hybrid nanoparticles, anionic ligand citrate stabilized AuNPs were used. This allowed an effective binding between the positively charged $NH_2$ groups of the polymeric ZnPc-Poly-nanoparticles and the negatively charged citrate groups of the AuNPs. The formation of these hybrid Au—ZnPc-Poly-NPs was evident from the DLS measurement, which showed a change in the zeta potential of the polymeric nanoparticles from positive to a negative value (FIG. 4D, right). The addition of ZnPc-Poly-NPs to AuNPs did not cause any aggregation (FIG. 4A).

The AuNP surface was modified with CpG-ODN with a 5'-modified —SH group (Dhar et al., (2009) *J. Am. Chem. Soc.* 131: 14652-14653). High concentrations of CpG-ODN could be loaded on the AuNP surface, as evident from the UV-Vis study. CpG-ODN adsorption stabilizes the hybrid nanoparticles and the steric repulsion of the nanoparticles prevents flocculation as evident from the decrease in size and PDI (FIG. 4A). Negative zeta potential of Au—ZnPc-Poly-NPs decreased with the formation of CpG-ODN-Au—ZnPc-Poly-NPs.

In Vitro Stability of the Hybrid Nanoparticles:: In vitro stability of nanoparticles can be defined relative to changes in hydrodynamic size and surface charge in response to changes in the sample environment. The key physicochemical properties, nanoparticle size, surface zeta potential, and morphology determine the in vivo stability profiles. The short-term stability of an aqueous suspension of CpG-ODN-Au—ZnPc-Poly-NPs was checked by storing at 4° C. for 30 days and evaluating the size distribution and zeta potential, as shown in Table 2.

TABLE 2

Stability of CpG—ODN—Au—ZnPc-Poly-NPs by dynamic light scattering measurements in nanopure water

|  | Hydrodynamic diameter (nm) | PDI | Zeta Potential (mV) |
|---|---|---|---|
| Day 1 | 186.0 ± 4.5 | 0.53 ± 0.07 | −10.6 ± 0.4 |
| Day 30 | 90.0 ± 0.4 | 0.42 ± 0.01 | −20.5 ± 0.3 |

The diameter of the hybrid nanoparticles decreases day after day. The mean size decreased from 186 nm to about 90 nm after 30 days and the surface charge changes from approximately −10 mV to −20 mV (Table 2).

Example 14

In Vitro Phototoxicity on Metastatic Breast Cancer Cells: The photodynamic activities of ZnPc-Poly-NPs, Au—ZnPc-Poly-NPs, and CpG-ODN-Au—ZnPc-Poly-NPs were investigated against 4T1 cell line using a 660 nm laser. In parallel, cells were incubated with all the constructs without illumination to serve as dark controls (FIGS. 5A and 5B). None of these constructs show any phototoxicity in the dark. The induction of cell death was both light and ZnPc-dose dependent. Two hours following the incubations, cells were illuminated with a 660 nm LASER light for 5 min per well. The mortality of post-PDT cultures was determined following the MTT assay. A higher phototoxic effect was observed with CpG-ODN-Au—ZnPc-Poly-NPs (IC50; 2.8 nM) than the ZnPc-Poly-NPs (IC50; 15 nM), Au—ZnPc-Poly-NPs (IC50; 6 nM) or free ZnPc (IC50; 317 nM) (FIGS. 5A and B). Control cells incubated with unconjugated AuNPs did not display any significant cell death after illumination.

Thus, under these in vitro conditions the possibility that any case of cell death is due to the photothermal activity of the AuNPs is minimized.

The efficacy of free ZnPc was lower than that for hybrid nanoparticles containing ZnPc in the polymeric core and CpG-ODN immobilized on the AuNP surface. While not wishing to be bound to any one theory, this enhancement in photodynamic efficacy is likely a consequence of synergistic effect between ZnPc and CpG-ODN when delivered in a single construct.

Example 15

In Vitro Antitumor Immunity after PDT: Bone marrow-derived immature DCs isolated from C57BL/6 mice were incubated with CpG-ODN or with LPS, a TLR4 agonist generally employed as a positive factor to stimulate and activate DCs, as positive controls and with photodynamic therapy killed 4T1 cell lysates. ELISA analysis was used to assess the immune response by measuring the levels of several proinflammatory cytokines (FIGS. 6A and 6B).

Figure 9A:
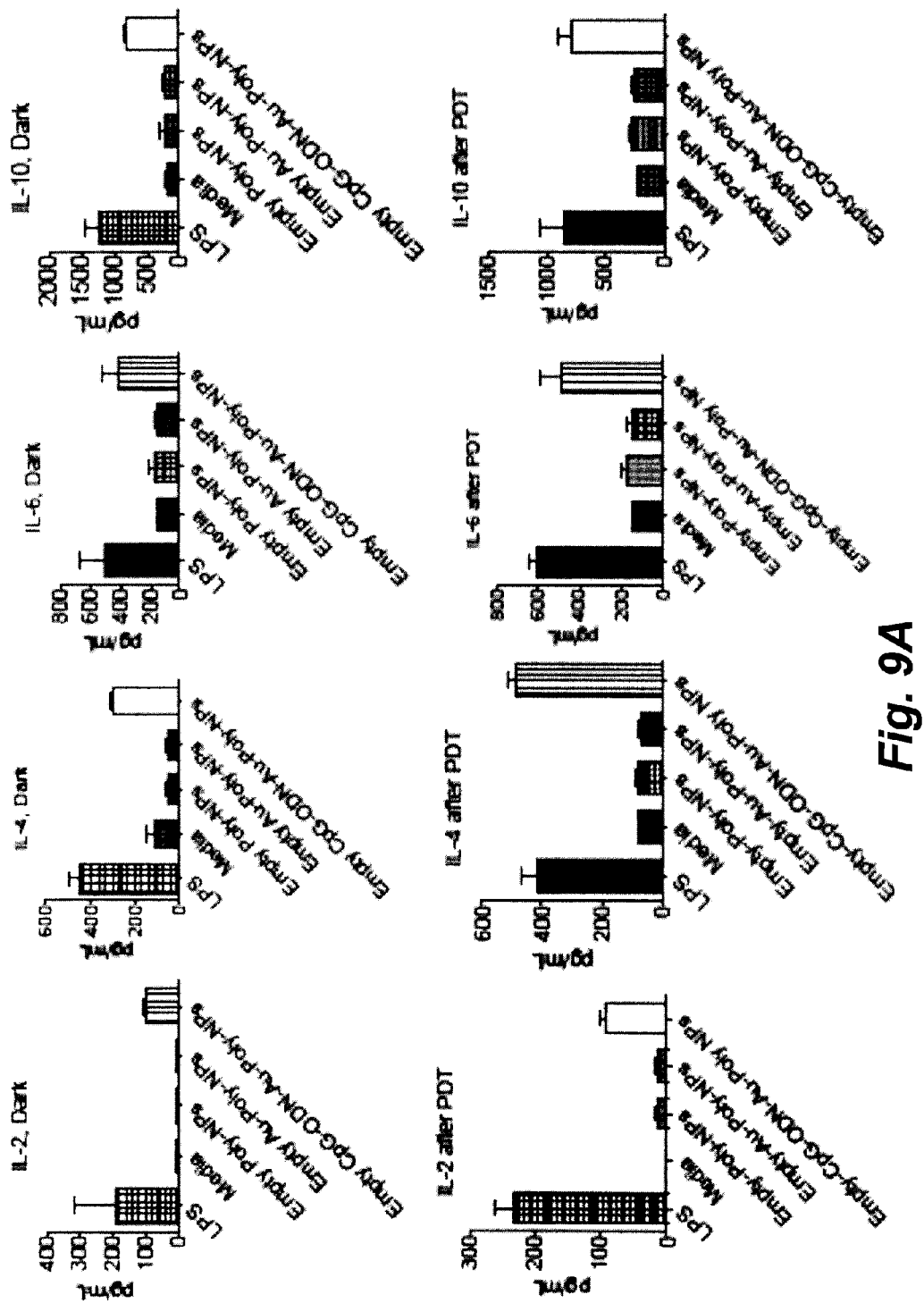
FIGS. 9A and 9B show a series of bar graphs illustrating in vitro antitumor immunity after photodynamic therapy with various control nanoparticles without encapsulated ZnPc by using ELISA.
Figure 9B:
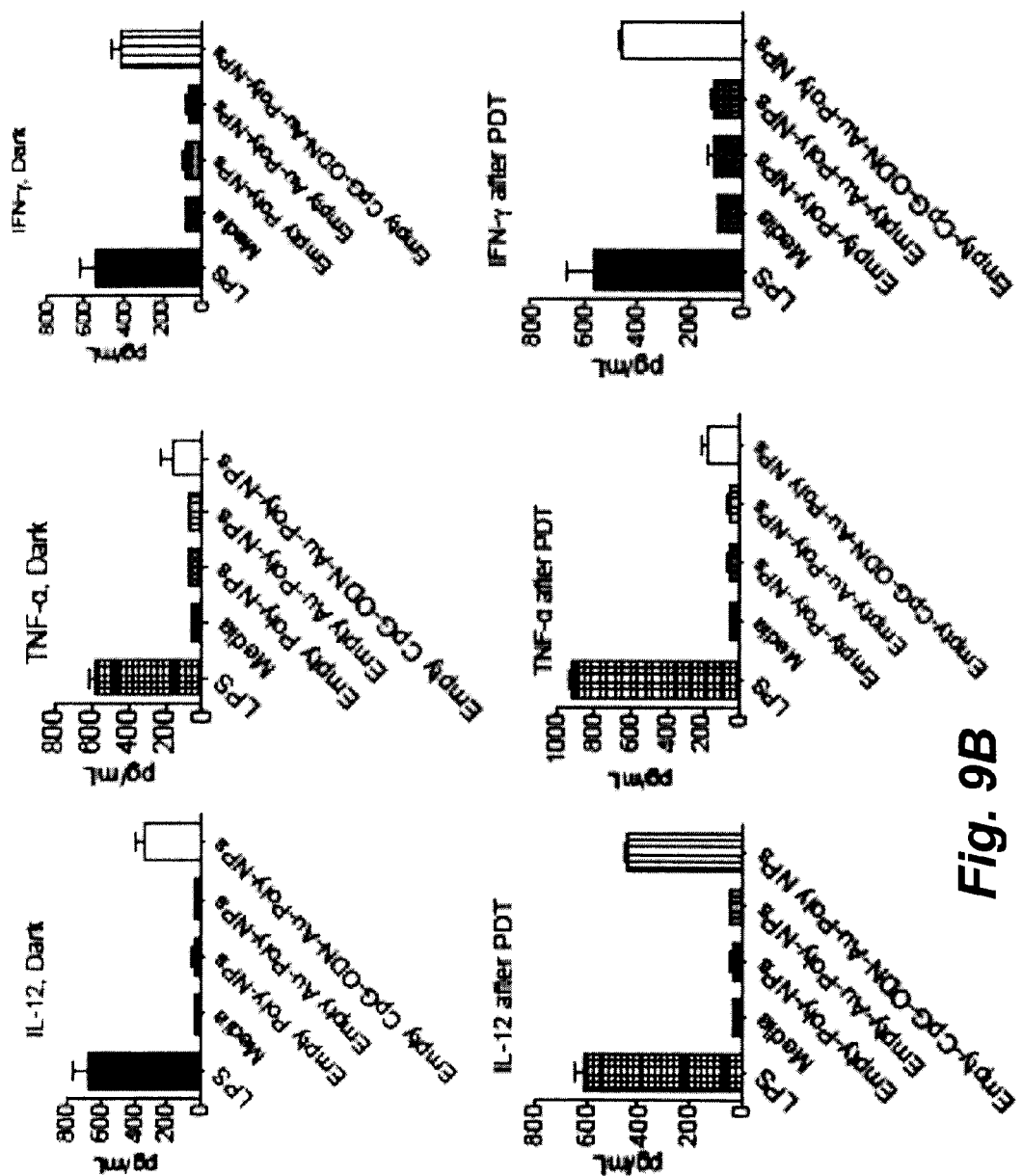

When CpG-ODN-Au—ZnPc-Poly-NP treated photodynamic therapy killed 4T1 tumor cell lysate was incubated with DCs, there was a synergistic increase in the production of IL-2, IL-6, IL-12, and TNF-α and these levels were either comparable or above the level of activation achieved with LPS (FIGS. 6A and 6B). However when a combination of free CpG-ODN and ZnPc, or ZnPc-Poly-NP treated photodynamic therapy killed 4T1 cell lysates were incubated with DCs, all the cytokine levels were below than the levels observed for CpG-ODN-Au—ZnPc-Poly-NPs. CpG-ODN alone had only a slight effect in secretion of these cytokines. These data suggest that a combination of CpG-ODN and a photosensitizer in a single NP construct can prime DC to recognize and phagocytosize photodynamic therapy killed tumor cells, and that this phagocytosis can lead to DC maturation and activation. The nanoparticles of the disclosure can cause activation of a specific and systemic immune response after photodynamic therapy that may result in further destruction of remaining local tumor cells and the prevention of possible recurrence. The antitumor efficacy of photodynamic therapy was further enhanced through an effective immunoadjuvant CpG-ODN to expand its usefulness for a possible control of distant metastasis. The concentrations of other cytokines, IL-4, IL-10, and IFN-γ were not changed compared with those of dark controls. Control experiments with various nanoparticles without encapsulated ZnPc showed no significant activation after photodynamic therapy or in the dark except for empty-CpG-ODN-Au-Poly-NPs, which showed immune response comparable to free CpG-ODN (FIGS. 9A and 9B).

We claim:

1. A multifunctional hybrid nanoparticle, comprising a nanoparticle core comprising a photosensitizer and a polymer, a plurality of metallic nanoparticles disposed on the surface of the nanoparticle core, and an immunostimulant disposed on the plurality of metallic nanoparticles, wherein the photosensitizer is zinc phthalocyanine, the nanoparticle core comprises a biodegradable polymer of poly (D,L-lactic-co-glycolic acid)-b-poly(ethylene glycol), the metallic nanoparticles are gold nanoparticles, and the immunostimulant disposed on the metallic nanoparticles is a CpG-ODN.

2. A method of reducing the viability of a cell comprising the steps of:
   (i) administering to an animal or human subject a pharmaceutically acceptable composition comprising a multifunctional hybrid nanoparticle comprising a nanoparticle core comprising a photosensitizer and a polymer, a plurality of metallic nanoparticles disposed on the surface of the nanoparticle core; and an immunostimulant disposed on the metallic nanoparticles, and wherein the immunostimulant generates an immune response in the animal or human subject that reduces the viability of a cancerous cell or a tumor, wherein the photosensitizer is zinc phthalocyanine, the nanoparticle core comprises a biodegradable polymer of poly (D,L-lactic-co-glycolic acid)-b-poly(ethylene glycol), the metallic nanoparticles are gold nanoparticles, and the immunostimulant disposed on the metallic nanoparticles is a CpG-ODN; and (ii) irradiating the cell with a light energy having a wavelength generating a photoacitvated oxygen species by the photosensitizer.

3. A pharmaceutically acceptable composition comprising a multifunctional hybrid nanoparticle comprising a nanoparticle core comprising a photosensitizer and a polymer; a plurality of a metallic nanoparticle disposed on the surface of the nanoparticle core; and an immunostimulant disposed on the surfaces of the plurality of metallic nanoparticles, wherein the photosensitizer is zinc pthalocyanine, the nanoparticle core comprises a biodegradable polymer of poly (D,L-lactic-co-glycolic acid)-b-poly(ethylene glycol), the metallic nanoparticles are gold nanoparticles, and the immunostimulant disposed on the metallic nanoparticles is CpG-ODN; and a pharmaceutically acceptable carrier.

* * * * *